United States Patent [19]

Haskell et al.

[11] 4,311,699

[45] Jan. 19, 1982

[54] AMINOACID DERIVATIVES OF CEPHALOSPORIN COMPOUNDS

[76] Inventors: Theodore H. Haskell, 3860 Loch Alpine Dr. W.; Thomas F. Mich, 915 Sunset Rd., both of Ann Arbor, Mich. 48103; Joseph P. Sanchez, 739 Meadowlake Rd., Canton, Mich. 48188; Dietrich Schweiss, 7136 Plymouth Rd., Ann Arbor, Mich. 48105

[21] Appl. No.: 112,656

[22] Filed: Jan. 31, 1980

Related U.S. Application Data

[63] Continuation-in-part of Ser. No. 19,992, Mar. 12, 1979.

[51] Int. Cl.³ .................. A61K 31/545; C07D 501/34; C07D 501/56
[52] U.S. Cl. ...................................... 424/246; 544/22; 544/27; 544/28; 544/319
[58] Field of Search ............................ 544/28, 22, 27; 424/246

[56] References Cited

U.S. PATENT DOCUMENTS 4,156,724 5/1979 Yamada et al. ...................... 544/27

Primary Examiner—Paul M. Coughlan, Jr.

[57] ABSTRACT

Novel organic amide compounds which are N-[2-[(acylaminoacylamino or aminoacylamino)phenyl]-4-hydroxy-5-pyrimidinylcarbonyl]cephalosporin compounds having broad spectrum antibacterial utility are provided by (a) reacting the free amino acid of the appropriate cephalosporin or the acid salt or silylated derivative or complex thereof with a reactive derivative of the corresponding N-2-[(acylaminoacylamino or aminoacylamino)phenyl]-4-hydroxy-5-pyrimidine carboxylic acid or (b) reacting the free amino acid 7-aminocephalosporanic acid or a related compound or the acid salt or silylated derivative thereof with a reactive derivative of the corresponding D-N-[2-[(acylaminoacylamino or aminoacylamino)phenyl]-4-hydroxy-5-pyrimidinylcarbonyl]-2-substituted glycine. Pharmaceutical compositions containing said compounds and methods for treating infections using said compositions are also disclosed.

51 Claims, No Drawings

AMINOACID DERIVATIVES OF CEPHALOSPORIN COMPOUNDS

This is a continuation-in-part of copending United States Application, Ser. No. 19,992, filed Mar. 12, 1979.

SUMMARY AND DETAILED DESCRIPTION

The present invention relates to novel chemical compounds that are useful as pharmacological agents and to methods for their production. More particularly, the invention relates to novel organic amide compounds having the formula

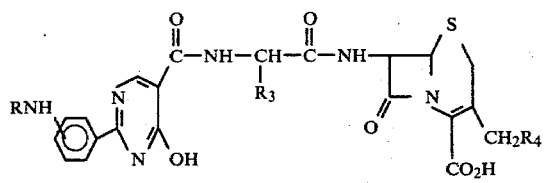

and pharmaceutically-acceptable salts thereof; wherein R is

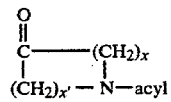

or $R_1[NR_5\text{-acyl}]_n$; x is an integer of from one to five; x' is zero, one or two, $R_1$ is hydrogen, lower alkyl, benzyl or

wherein $R_2$ is hydrogen, amino or a lower alkyl group of from one to four carbon atoms, optionally substituted by from one to three chlorine or fluorine atoms, $R_5$ is hydrogen or lower alkyl and N-acyl is an aminoacyl moiety derived from a carboxylic acid of from two to ten carbon atoms optionally substituted by from one to three of the following groups, hydroxyl, carboxyl,

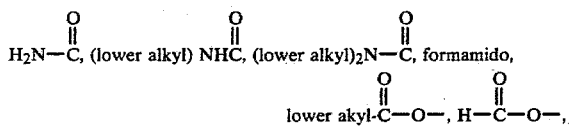

amino, lower alkylamido carbamido, carbonyl oxygen, lower alkoxy, lower alkylthio, or sulfonic acid; n is an integer of from one to four; $R_3$ is phenyl, 4-hydroxyphenyl, 2-thienyl or cyclohexa-1,4-dien-1-yl and $R_4$ is acetoxy, carbamoyloxy or a heterocyclicthio group where the heterocyclic moiety is an optionally methyl substituted thiadiazolyl, triazolyl or tetrazolyl group or the hetercyclicthio group has the formula

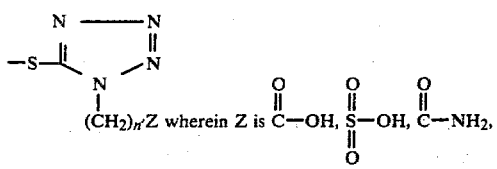

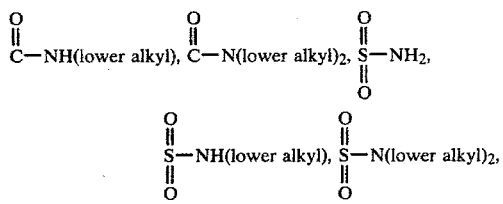

or $CH_2\text{-OH}$ and n' is an integer of from one to four.

When n is two to four, the acyl groups may be the same or different. When the acyl group is substituted by more than one group, the substituents may be the same or different.

Included within the above definition for N-acyl are cyclic structures incorporating the nitrogen atom by removal of two hydrogen atoms, such as the pyroglutamyl group, prolyl group, etc.

The carbon atoms may be a part of a configuration which is classified as an aliphatic, olefinic or aromatic grouping or mixture of both, such as a phenethyl group.

The term "lower alkyl", where not specifically defined, is intended to mean a hydrocarbon moiety having from one to six carbon atoms. Lower alkoxy is equivalent to "lower alkyl-O-".

The preferred compounds are those wherein R-NH is in the para position. The most preferred compounds are those wherein N-acyl is D-alanyl, L-alanyl, DL-glutaminyl, L-hydroxyprolyl, DL-lysyl; $R_2$ is a carbon fragment of from one to four carbon atoms, $R_3$ is phenyl or p-hydroxyphenyl, $R_4$ is acetoxy or a heterocyclicthio group wherein the heterocyclic group is a tetrazole and n is one and Z is hydrogen or carboxyl; and pharmaceutically-acceptable salts thereof.

In accordance with the invention the foregoing amide compounds having the formula

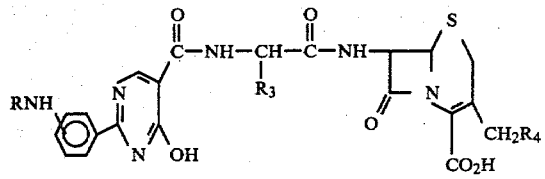

and pharmaceutically salts thereof wherein R, $R_1$, $R_2$, $R_3$ $R_4$ and $R_5$ are as previously defined are produced by reacting a compound of the formula

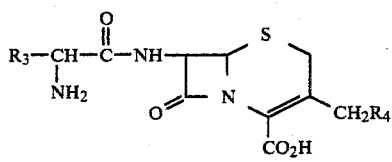

or the basic salt, silylated derivative (preferably the disilylated) thereof wherein $R_3$ and $R_4$ are as previously defined, with a reactive derivative of a 4-hydroxy-5-pyrimidine carboxylic acid compound having the formula

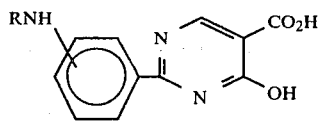

or its acid addition salt, where R, $R_1$ and $R_2$ all have the aforementioned significance.

Some examples of reactive derivatives of the 2-(substituted)-4-hydroxy-5-pyrimidine carboxylic acid compound suitable for the reaction are the acid halides (especially the acid chloride), the imidazolide, mixed anhydrides (especially those formed from an alkyl chloroformate, such as methyl, ethyl, and isobutyl chloroformate or pivaloyl chloride), and activated esters, such as the pentachlorophenyl ester and N-hydroxysuccinimide ester.

The reactants are normally employed in approximate equimolar quantities, although an excess of either (pyrimidine acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the cephalosporin compounds in the zwitter ionic salt form, aqueous solutions may be used for acylation with an acid halide or mixed anhydride under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of 2-(substituted)-pyrimidine carboxylic acid compounds and acid-addition salts which are required as starting materials in the foregoing process can be prepared according to any of a variety of methods.

A 2-(substituted)-4-hydroxy-5-pyrimidine carboxylic acid may be converted to its acid chloride utilizing thionyl chloride, its mixed anhydride utilizing ethyl chloroformate, its pentachlorophenyl ester by esterification with pentachlorophenol in the presence of dicyclohexylcarbondiimide and its imidazolide by reacting the acid with 1,1'-carbonyldiimidazole.

Compounds of the formula

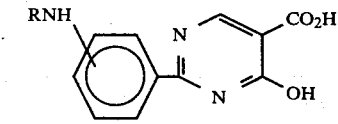

except wherein. R is H[NH-acyl]n, are prepared by acylation of a compound of the formula

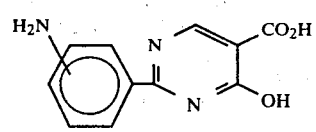

with a compound of the formula

R-OH wherein R is as previously defined, except where R is H[NH-acyl]n

The compound of the formula

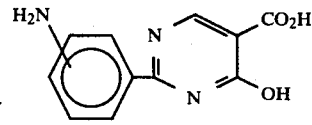

is prepared by hydrolyzing a compound of the formula

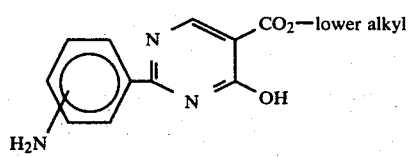

which is in turn prepared by coupling a compound of the formula

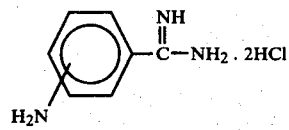

with a compound of the formula lower alkyl-O-CH=C(CO$_2$-lower alkyl)$_2$

The compound of the formula

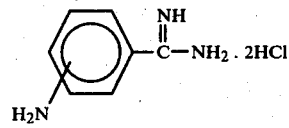

is prepared by reducing a compound of the formula

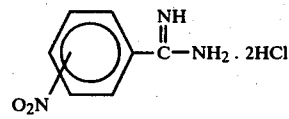

The silylated amino acid starting materials can be prepared by reacting an amino acid of the formula.

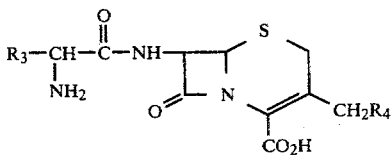

or a salt thereof wherein $R_3$ and $R_4$ are as previously defined in anhydrous form with either one or two equivalents of a tri(lower alkyl)silyl chloride in the presence of triethylamine. The preferred silylating agents are trimethylsilyl chloride and dimethyldichlorosilane. In all probability when two equivalents of the silylating agent are used, both the amino and the carboxyl group become silylated. When one equivalent is used; only the carboxyl group is silylated. Both the mono-and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

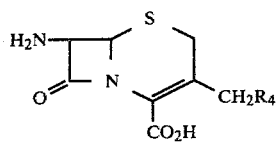

or the corresponding acid salt or silylated derivative thereof with a reactive derivative of D-N-[2-(substituted)-4-hydroxy-5-pyrimidinylcarbonyl]-2-substituted glycine having the formula

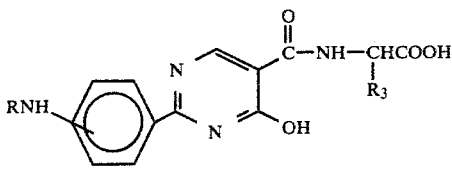

or its acid addition salts where R, $R_1$, $R_2$, $R_3$, $R_4$ and $R_5$ have the aforementioned significance.

Some examples of reactive derivatives of the D-N-(4-hydroxy-5-pyrimidinylcarbonyl)-2-substituted glycine compounds suitable for the reaction are the acid halides, mixed anhydrides (especially those formed from an alkyl chloroformate, such as ethyl chloroformate and isobutyl chloroformate), and activated esters, such as the pentachlorophenyl ester and N-hydroxysuccinimide ester. Since racemization is more likely with the acid halide, the other forms are generally preferred. The reactants are normally employed in approximate equimolar quantities, although an excess of either (pyrimidine acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 7-aminocephalosporanic acid may be reacted with an acid chloride or mixed anhydride in the free acid or salt form using aqueous solutios under normal Schotten-Baumann conditions. The duration and temperature of the reaction are not critical. Temperatures in the range from −30° to +30°C. are commonly used for reaction times ranging from a few hours up to a day or more. The product may be isolated in any suitable way as the free acid or as a salt by appropriate adjustment of the pH.

The reactive derivative of D-N-[2-(substituted)-4-hydroxy-5-pyrimidinylcarbonyl]-2-substituted glycines or their acid-addition salts which are required as starting materials in the foregoing process can be prepared by methods illustrated in greater detail hereinafter.

D-N-[2-(substituted)-4-hydroxy-5-pyrimidinylcarbonyl]-2-substituted glycine compounds may be prepared by reacting the corresponding reactive derivative of 2-(substituted)-4-hydroxy-5-pyrimidine carboxylic acid, such as acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

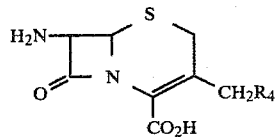

with a hexaalkyldisilazane. The preferred silylating agent is hexamethyldisilazane. In all probability, only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically-acceptable carboxylate salts are formed by reacting the free acids with such bases as sodium hydroxide, sodium carbonate, sodium bicarbonate, sodium-2-ethylhexanoate, potassium hydroxide, potassium carbonate, potassium-2-ethylhexanoate, lithium hydroxide, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. Certain compounds are capable of forming di-salts, which is dependent upon the final pH of the solution. In addition, certain of the compounds of the invention can exist in the form of an acid-addition salt. Pharmaceutically-acceptable salts are formed by reaction of the free base of a carboxylate salt (zwitter ion) with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic, and related acids.

The compounds of the invention can exist in anhydrous form, as well as in solvated, including hydrated, forms. In general, the hydrated forms and the solvated forms with pharmaceutically-acceptable solvents are equivalent to the anhydrous or unsolvated forms for the purposes of the invention.

The pyrimidine segment of the compounds of this invention may be capable of undergoing keto-enol tautomerism to give 4-keto or 4-hydroxy forms. Such a keto tautomer is equivalent to the shown 4-hydroxy structures for the purposes of the inventions and is included within the above shown structures.

The compounds of the present invention can exist in various stereoisomeric forms. More specifically, the newly introduced amino acid fragments of the compounds may be in the form of the D-isomer, L-isomer or a mixture thereof [DL-mixture (partial or complete racemization)]. The invention is intended to include all of the isomeric forms and mixtures thereof. Even when a specific form is cited, small amounts of its stereoisomermay be present, since racemization may occur during the various steps in preparing the compound.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table.

Thus, the compounds of this invention and their non-toxic pharmaceutically-acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day; and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc. the preferred route of administration is parenterally for treating systemic infections.

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

ACTIVITY TABLE

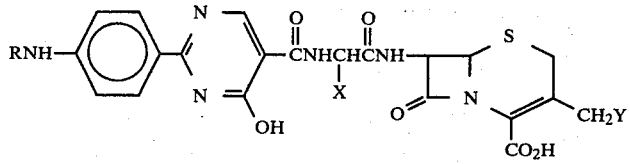

| | | | | Minimal Inhibitory Concentration (μg/ml) | | | | | | | | | | |
|---|---|---|---|---|---|---|---|---|---|---|---|---|---|---|
| | | | | Pseudo-monas BRK | UI | E. coli | | Prot | Entero. | Serr. | Klebs. | Strep. | Staph. aureus | |
| EX. | R | X | Y | #28 | 12-4-4 | 18 | Brig | Vogel | vulg. | cloacae | marces. | pneu. | fec. | UC-76 | S18733 |
| 1 | Ac—D—Ala | A | D | 3.1 | 3.1 | 3.1 | 25 | 6.3 | 12.5 | 50 | 12.5 | 200 | 50 | 0.8 | 3.1 |
| 2 | AcNHC(CH3)2C(=O) | A | D | 1.6 | 6.3 | 3.1 | 50 | 25 | 25 | 50 | >50 | 25 | >50 | 3.1 | 12.5 |
| 3 | AcNH(CH2)2C(=O) | A | D | 6.3 | 12.5 | 6.3 | 25 | 12.5 | 12.5 | 50 | <50 | 12.5 | 50 | 1.6 | 6.3 |
| 4 | Ac—DL—Leu | A | D | 12.5 | 12.5 | 12.5 | 25 | 6.3 | 25 | 25 | >50 | 25 | 50 | 1.6 | 6.3 |
| 5 | Ac—DL—Met | A | D | 3.1 | 6.3 | 12.5 | 25 | 6.3 | 25 | 25 | >50 | 12.5 | 50 | 1.6 | 3.1 |
| 6 | DL—Glu | A | D | 6.3 | 12.5 | 12.5 | 50 | 12.5 | 50 | 50 | >50 | 25 | 50 | 1.6 | 6.3 |
| 7 | Ac—Gly | A | D | | | 12.5 | | | | 25 | | 6.3 | 50 | | |
| 8 | Ac—DL—Ala | A | D | 6.3 | 12.5 | 6.3 | 25 | 6.3 | 50 | 50 | >50 | 6.3 | 50 | 1.6 | 1.6 |
| 9 | Ac—DL—Ala | B | D | 1.6 | 3.1 | 3.1 | 50 | 12.5 | 12.5 | 50 | >50 | 12.5 | 50 | 3.1 | 6.3 |
| 10 | Ac—L—Ala | A | D | 6.3 | 12.5 | 6.3 | 25 | 12.5 | 25 | 50 | >50 | 25 | 50 | 3.1 | 6.3 |
| 11 | Ac—D—Ala | B | D | 3.1 | 6.3 | 6.3 | 50 | 6.3 | 12.5 | 50 | >50 | 25 | 50 | 6.3 | 25 |
| 12 | Diac—DL—Lys | A | D | 6.3 | 12.5 | 6.3 | 50 | 6.3 | 50 | 25 | >50 | 25 | 50 | 1.6 | 6.3 |
| 13 | Ac—DL—Pro | A | D | 6.3 | 12.5 | 12.5 | 50 | 12.5 | 50 | 50 | >50 | 25 | 50 | 3.1 | 6.3 |
| 14 | Ac—DL—Gln | A | D | 6.3 | 12.5 | 12.5 | 25 | 6.3 | 25 | 50 | >50 | 12.5 | 50 | 1.6 | 6.3 |
| 15 | Ac—L—Hypro | A | D | 3.1 | 12.5 | 3.1 | 50 | 6.3 | 50 | >50 | >50 | 12.5 | 25 | 1.6 | 6.3 |
| 16 | AcNH(CH2)3C(=O) | A | D | 6.3 | 12.5 | 12.5 | 50 | 6.3 | 25 | 25 | >50 | 12.5 | 25 | 0.8 | 3.1 |
| 17 | Ac—D—Val | A | D | 6.3 | 12.5 | 6.3 | 12.5 | 6.3 | 25 | 25 | >50 | 12.5 | 50 | 1.6 | 6.3 |
| 18 | D—Ala | A | D | 3.1 | 6.3 | 1.6 | 50 | 12.5 | 25 | 50 | >50 | 25 | 25 | 1.6 | 6.3 |
| 19 | Ac—D—Ala | C | D | 6.3 | 6.3 | 6.3 | >50 | 12.5 | 25 | 50 | >50 | 12.5 | 25 | 0.8 | 1.6 |
| 20 | Ac—DL—Ala | A | E | 6.3 | 12.5 | 6.3 | 50 | 12.5 | 25 | >50 | >50 | 25 | >50 | 1.6 | 3.1 |
| 21 | Ac—D—Ala | A | E | 3.1 | 12.5 | 12.5 | 25 | 12.5 | 12.5 | 25 | >50 | 12.5 | 25 | 0.8 | 1.6 |
| 22 | Ac—Gly | A | F | 6.3 | 12.5 | 12.5 | 6.3 | 0.8 | 6.3 | 6.3 | 50 | 0.8 | 50 | 1.6 | 3.1 |
| 23 | Ac—DL—Gln | A | F | 6.3 | 12.5 | 6.3 | 3.1 | 0.8 | 12.5 | 6.3 | 50 | 3.1 | 50 | 3.1 | 12.5 |
| 24 | Ac—DL—Ala | A | F | 6.3 | 12.5 | 6.3 | 12.5 | 3.1 | 25 | 12.5 | 50 | 1.6 | 50 | 1.6 | 3.1 |
| 25 | Ac—D—Ala | A | F | 3.1 | 6.3 | 6.3 | 6.3 | 3.1 | 12.5 | 6.3 | 50 | 3.1 | >50 | 1.6 | 6.3 |
| 26 | Ac—L—Ala | A | F | 6.3 | 12.5 | 12.5 | 12.5 | 3.1 | 12.5 | 12.5 | 50 | 6.3 | 50 | 6.3 | 12.5 |

ACTIVITY TABLE-continued

| | | | | | Minimal Inhibitory Concentration (μg/ml) | | | | | | | | | |
|---|---|---|---|---|---|---|---|---|---|---|---|---|---|---|
| | | | | | Pseudo-monas BRK | UI | E. coli | | Prot | Entero. | Serr. | Klebs. | Strep. | Staph. aureus | |
| EX. | R | X | Y | #28 | 12-4-4 | 18 | Brig | Vogel | vulg. | cloacae | marces. | pneu. | fec. | UC-76 | S18733 |
| 27 | AcNH(CH₂)₃C(O)- | A | F | 3.1 | 12.5 | 6.3 | 12.5 | 1.6 | 12.5 | 6.3 | 25 | 1.6 | 25 | 1.6 | 6.3 |
| 28 | ACNHC(CH₃)₂C(O)- | A | F | 3.1 | 6.3 | 6.3 | 12.5 | 3.1 | 25 | 6.3 | 50 | 6.3 | 50 | 3.1 | 6.3 |
| 29 | Ac—D—Val | A | F | 6.3 | 12.5 | 6.3 | 12.5 | 1.6 | 6.3 | 12.5 | 50 | 3.1 | 25 | 1.6 | 3.1 |
| 30 | Ac—L—Hypro | A | F | 6.3 | 12.5 | 6.3 | 12.5 | 3.1 | 25 | 6.3 | >50 | 3.1 | >50 | 3.1 | 12.5 |
| 31 | Ac—D—Ala | B | F | 3.1 | 3.1 | 3.1 | 6.3 | 1.6 | 6.3 | 6.3 | 50 | 1.6 | 25 | 3.1 | 6.3 |
| 32 | Ac—DL—Ala | B | F | 3.1 | 6.3 | 6.3 | 6.3 | 1.6 | 6.3 | 12.5 | >50 | 1.6 | 50 | 3.1 | 6.3 |
| 33 | Ac—L—Ala | A | G | 6.3 | 12.5 | 12.5 | 12.5 | 1.6 | 3.1 | 6.3 | >50 | 6.3 | >50 | 6.3 | 25 |
| 34 | Ac—D—Ala | A | G | 12.5 | 12.5 | 12.5 | 12.5 | 3.1 | 1.6 | 12.5 | >50 | 6.3 | >50 | 12.5 | 25 |
| 35 | Ac—DL—Ala | A | G | 6.3 | 12.5 | 12.5 | 6.3 | 3.1 | 3.1 | 6.3 | 50 | 6.3 | >50 | 12.5 | 25 |
| 36 | Ac—L—Hypro | A | G | 12.5 | 12.5 | 12.5 | 12.5 | 6.3 | 6.3 | 12.5 | 50 | 6.3 | >50 | 12.5 | 25 |
| 37 | Ac—D—Ala | B | G | 12.5 | 12.5 | 6.3 | 12.5 | 3.1 | 1.6 | 12.5 | >50 | 12.5 | >50 | 25 | 25 |
| 38 | D—Ala | A | G | 3.1 | 3.1 | 3.1 | 6.3 | 0.8 | 0.8 | 6.3 | 25 | 6.3 | >50 | 6.3 | 12.5 |
| 39 | Ac—Gly | A | H | 12.5 | 25 | 25 | 12.5 | 1.6 | 6.3 | 6.3 | 50 | 1.6 | 50 | 0.8 | 3.1 |
| 40 | Ac—DL—Ala | A | H | 12.5 | 12.5 | 6.3 | 12.5 | 3.1 | 50 | 25 | 50 | 3.1 | 25 | 0.4 | 3.1 |
| 41 | L—Gln | A | G | 12.5 | 12.5 | 12.5 | 12.5 | 3.1 | 1.6 | 12.5 | 50 | 3.1 | >50 | 12.5 | 25 |
| 42 | pyrrolidinone-N—CH₂C(O)- | A | G | 6.3 | 12.5 | 6.3 | 6.3 | 3.1 | 1.6 | 6.3 | 50 | 3.1 | >50 | 12.5 | 25 |

A = 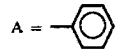 —phenyl

B =  —OH (hydroxyphenyl)

C = 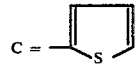 (thienyl)

D = —OAc

E = —OCONH₂

F = 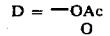 —S-(1-methyltetrazolyl)

G = 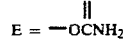 —S-(1-carboxymethyltetrazolyl, Na salt)

H = 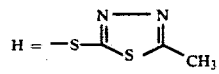 —S-(5-methyl-1,3,4-thiadiazolyl)

EXAMPLE 1

N-[2-[4-(N-Acetyl-D-alanylamino)phenyl]-4-hydroxy-5-pyrimidinyl-carbonyl]-7-[D-2-amino-2-phenylacetamido]-3-acetoxymethyl-3-cephem-4-carboxylic acid A suspension of 4.1 g (10 mmol) of cephaloglycin and 50 ml of N,N-dimethylacetamide is stirred in an ice bath and 3.55 g (9 mmol) of 2-[4-(N-acetyl-D-alanylamino)-phenyl]-4-hydroxy-5-pyrimidine carboxylic acid imidazolide is added followed by 1.4 ml (10 mmol) of triethylamine. The ice bath is removed and the reaction mixture stirred at room temperature for 3 hrs and filtered. The filtrate is cooled in to 0°-5°* and 3.1 ml (9 mmol) of 2.9 M sodium 2-ethylhexanoate in N,N-dimethylacetamide is added. The solution is then added dropwise with stirring to 800 ml of ice cooled ethyl acetate. The precipitated solid is filtered, washed with ether, and dissolved in 100 ml cold water. The pH is adjusted to 2.5 with 1 N hydrochloric acid and the solid is filtered, suspended in 250 ml of ice water, stirred for 20 min and filtered. The filter cake is resuspended in 100 ml of cold water and the pH adjusted to 6.5 with 1 N sodium hydroxide. Filtration and lyophilization gives 5.9 of the sodium salt of the title cephalosporin; $[\alpha]_D^{23} + 83°$ (c1, pH 7).

$$E_1^1 \begin{array}{cc} 297 & \lambda\ 316\ nm \\ 234 & 272\ nm \end{array} pH\ 7$$

*All temperatures are stated in degrees Centigrade.

EXAMPLE 2

N-[2-[4-(N-Acetyl-alpha-aminoisobutyrylamino)-phenyl]-4-hydroxy-5-pyrimidinylcarbonyl]-7-[D-2-amino-2-phenylacetamido]-3-acetoxymethyl-3-cephem-4-carboxylic acid Using the method of Example 1, 2.9 g (7 mmol) of cephaloglycin, 2.3 g (5.8 mmol) of 2-[4-(N-acetyl-alpha-aminoisobutyrylamino)phenyl]-4-hydroxy-5-pyrimidine carboxylic acid imidazolide, 30 ml of N,N-dimethylacetamide, and 0.85 ml (6 mmol) of triethylamine are allowed to react for 2 hrs. Work up and lyophilization of a pH 6.0 solution gives 3.0 g of the sodium salt of the title cephalosporin; $[\alpha] + 48.5°$ (c1, pH 7).

$$E_1^1 \begin{array}{cc} 288 & \lambda\ 316\ nm \\ 228 & 270\ nm \end{array} pH\ 7$$

EXAMPLE 3

N-[2-]4-(N-Acetyl-beta-alanylamino)phenyl]-4-hydroxy-5-pyrimidinylcarbonyl]-7-[D-2-amino-2-phenylacetamido]-3-acetoxymethyl-3-cephem-4-carboxylic acid Using the method of Example 1, 2.7 g (6.5 mmol) of cephaloglycin, 2.3 g (5.8 mmol) of 2-[4-(N-acetyl-beta-alanylamino)phenyl]-4-hydroxy-5-pyrimidine carboxylic acid imidazolide, 30 ml of N,N-dimethylacetamide, and 0.85 ml (6 mmol) of triethylamine are allowed to react for 3 hrs. Work up and lyophilization of pH 6.5 solution gives 3.14 g of the sodium salt of the title cephalosporin derivative; $[\alpha]_D^{23} + 14.2°$ (c1, 75% DMF/pyridine).

$$E_1^1 \begin{array}{cc} 323 & \lambda\ 317\ nm \\ 240 & 275\ nm \end{array} pH\ 7$$

EXAMPLE 4

N-[2-[4-(N-Acetyl-DL-leucylamino)phenyl]-4-hydroxy-5-pyrimidinylcarbonyl]-7-[D-2-amino-2-phenylacetamido]-3-acetoxymethyl-3-cephem-4-carboxylic acid Using the method of Example 1, 4.92 g (12 mmol) of cephaloglycin, 4.36 g (10 mmol) of 2-[4-(N-acetyl-DL-leucylamino)phenyl]-4-hydroxy-5-pyrimidine carboxylic acid imidazolide, 40 ml of N,N-dimethylacetamide, and 1.54 ml (11 mmol) of triethylamine are allowed to react for 4 hrs. Work up and lyophilization of pH 7 solution gives 6.28 g of the sodium salt of the title cephalosporin; $[\alpha]_D^{23} + 16°$ (c1, pH 7).

$$E_1^1 \begin{array}{cc} 322 & \lambda\ 317\ nm \\ 256 & 272\ nm \end{array} pH\ 7$$

EXAMPLE 5

N-[2-[4-(N-Acetyl-DL-methionylamino)phenyl]-4-hydroxy-5-pyrimidinylcarbonyl]-7-[D-2-amino-2-phenylacetamido]-3-acetoxymethyl-3-cephem-4-carboxylic acid Using the method of Example 1, 4.9 g (12 mmol) of cephaloglycin, 4.54 g (10 mmol) of 2-[4-(N-acetyl-DL-methionylamino)phenyl]-4--hydroxy-5-pyrimidine]carboxylic acid imidazolide, 50 ml of N,N-dimethylacetamide, and 1.4 ml (10 mmol) of triethylamine are allowed to react for 3 hrs. Work up and lyophilization of pH 7 solution gives 6.1 g of the sodium salt of the title cephalosporin; $[\alpha]_D^{23} + 21°$ (c1, pH 7).

$$E_1^1 \begin{array}{cc} 326 & \lambda\ 317\ nm \\ 258 & 272\ nm \end{array} pH\ 7$$

EXAMPLE 6

N-[2-]4-((5-oxo-DL-prolyl)amino)phenyl]-4-hydroxy-5-pyrimidinylcarbonyl]-7-[D-2-amino-2-phenylacetamido]-3-acetoxymethyl-3-cephem-4-carboxylic acid Using the method of Example 1, 2.3 g (5.5 mmol) of cephaloglycin, 1.9 g (5 mmol) of 2-[4-((5-oxo-DL-prolyl)-amino)phenyl]-4-hydroxy-5-pyrimidine carboxylic acid imidazolide, 30 ml of N,N-dimethylacetamide, and 0.7 ml (5 mmol) of triethylamine are allowed to react for 3 hrs. Work up and lyophilization of pH 6.5 solution gives 1.8 g of the sodium salt of the title cephalosporin derivative; $[\alpha]_D^{23} + 44°$ (c1, pH 7).

$$E_1^1 \begin{array}{cc} 344 & \lambda\ 315\ nm \\ 275 & 275\ nm \end{array} pH\ 7$$

EXAMPLE 7

N-[2-[4-(N-Acetylglycylamino)phenyl]-4-hydroxy-5-pyrimidinylcarbonyl]-7-[D-2-amino-2-phenylacetamido]-3-acetoxymethyl-3-cephem-4-carboxylic acid A suspension of 1.45 (3.5 mmol) of cephaloglycin, 15 ml of N,N-dimethylacetamide, and 1.2 ml (3.5 mmol) of 2.9 M sodium 2-ethylhexanoate is stirred at room temperature and 1.24 g (3.27 mmol) of 2-[4-(N-acetylglcylamino)phenyl]-4-hydroxy-5-pyrimidine carboxylic acid imidazolide is added. The reaction mixture is stirred at room temperature for 3 hrs and 100 ml of ethyl acetate is added. The precipitated solid is filtered, dissolved in 100 ml of water and the pH adjusted to 2.5 with 1N hydrochloric acid. The solids are filtered and washed with water and resuspended in water. The pH is raised to 7.8 with 1N sodium hydroxide and the solution lyophilized to give 2.5 g of the title cephalosporin derivative; $[\alpha]_D^{23} - 59°$ (c1, pH 7).

$$E_1^1 \begin{array}{cc} 247 & \lambda\ 272\ nm \\ 310 & 317\ nm \end{array} pH\ 7$$

EXAMPLE 8

N-[2-[4-(N-Acetyl-DL-alanylamino)phenyl]-4-hydroxy-5-pyrimidinylcarbonyl]-7-[D-2-amino-2-phenylacetamido]-3-acetoxymethyl-3-cephem-4-carboxylic acid Using the method of Example 7, 4.35 g (0.5 mmol) of cephaloglycin, 3.1 ml (10.2 mmol) of 3.3 M sodium 2-ethylhexanoate in N,N-dimethylacetamide, 3.94 g (10.0 mmol) of 2-[4-(N-acetyl-DL-alanylamino)phenyl]-4-hydroxy-5-pyrimidine carboxylic acid imidazolide, and 35 ml of N,N-dimethylacetamide are allowed to react. Work up and lyophilization of an aqueous solution gives 6.7 g of the sodium salt of the title cephalosporin compound; $[\alpha]_D^{23} + 33°$ (cl, pH 7)

$E_1^1 \ 243 \ \lambda \ 271 \ nm \atop 1 \ 309 \ \ \ \ 315 \ nm$ pH 7

EXAMPLE 9

N-[2-[4-(N-Acetyl-DL-alanylamino)phenyl]-4-hydroxy-5-pyrimidinylcarbonyl]-7-[D-2-amino-2-(4-hydroxyphenyl)acetamido]-3-acetoxymethyl-3-cephem-4-carboxylic acid A suspension of 2.22 g (4.13 mmol) of 7-[D-2-amino-2-(4-hydroxyphenyl)acetamido-3-acetoxymethyl-3-cephem-4-carboxylic acid trifluoroacetic acid salt [J. Antibiot., 29, 65 (1976)], 1.63 g (4.13 mmol) of 2-[4-(N-acetyl-DL-alanylamino)phenyl]-4-hydroxy-5-pyrimidine carboxylic acid imidazolide, 15 ml of N,N-dimethylacetamide, and 15 ml of dimethyl sulfoxide is stirred at room temperature and 1.25 ml (4.13 mmol) of 3.3 M sodium 2-ethylhexanoate in N,N-dimethylacetamide is added. Solution is observed in 10 min and the reaction mixture is allowed to stir at room temperature for 1.5 hrs. A 1.25 ml (4.13 mmol) portion of 3.3 M sodium 2-ethylhexanoate in N,N-dimethylacetamide is added and the solution is added dropwise to 400 ml of stirring ethyl acetate. The solid is filtered, washed with ethyl acetate, dried, and dissolved in 100 ml of ice water. The solution is acidified to pH 2.3 with 1N hydrochloric acid and the precipitated acid filtered and washed with ice water. The solid is suspended in ice water and dissolved by adjusting the pH to 7.5 with 1 N sodium hydroxide. Lyophilization gives 2.5 g of the sodium salt of the above named cephalosporin derivative; $[\alpha]_D^{23} + 19.5°$ (cl, pH 7).

$E_1^1 \ 308 \ \lambda \ 316 \ nm \atop 1 \ 246 \ \ \ \ 272 \ nm$ pH 7

EXAMPLE 10

N-[2-[4-(N-Acetyl-L-alanylamino)phenyl]-4-hydroxy-5-pyrimidinylcarbonyl]-7-[D-2-amino-2-phenylacetamido]-3-acetoxy-methyl-3-cephem-4-carboxylic acid A mixture of 1.06 g (2.6 mmol) of cephaloglycin, 10 ml of N,N-dimethylacetamide, and 1.03 g (2.6 mmol) of 2-[4-(N-acetyl-L-alanylamino)phenyl]-4-hydroxy-5-pyrimidine carboxylic acid imidazolide is stirred at room temperature for 4 hrs. The reaction is filtered and the filtrate cooled in an ice bath and 0.79 ml (2.6 mmol) of 3.3 M sodium 2-ethylhexanoate is added. The resulting solution is added to ethyl acetate and the solid filtered, washed with ethyl acetate, and air dried. The crude sodium salt is dissolved in water and the pH adjusted to 2.3 with 1N hydrochloric acid. The precipitate is filtered washed with water and resuspended in water. The pH is raised to 6.2 with 1N sodium hydroxide and the solution lyophilized to give 1.63 g of the sodium salt of the title cephalosporin; $[\alpha]_D^{23} + 4.3°$ (cl, pH 7).

$E_1^1 \ 267 \ \lambda \ 272 \ nm \atop 1 \ 328 \ \ \ \ 317 \ nm$ pH 7

EXAMPLE 11

N-[2-[4-(N-Acetyl-D-alanylamino)phenyl]-4-hydroxy-5-pyrimidinylcarbonyl]-7-[D-2-amino-2-(4-hydroxyphenyl)-acetamido]-3-acetoxymethyl-3-cephem-4-carboxylic acid Using the method of Example 10, 2.70 g (5 mmol) of 7-[D-2-amino-2-(4-hydroxyphenyl)acetamido]-3-acetoxymethyl-3-cephem-4-carboxylic acid trifluoroacetic acid salt [J. Antibiot., 29, 65 (1976)] 2.0 g (5 mmol) of 2-[4-(N-acetyl-D-alanylamino)-phenyl]-4-hydroxy-5-pyrimidine carboxylic acid imidazolide, and 35 ml of N,N-dimethylacetamide are allowed to react at room temperature for 3 hrs. Work up with 3.37 ml (11 mmol) of 3.3 M sodium 2-ethylhexanoate in N,N-dimethylacetamide and lyophilization of a pH 7.3 solution gives 3.45 g of the sodium salt of the title cephalosporin derivative; $[\alpha]_D^{23} + 42.8°$ (cl, pH 7).

$E_1^1 \ 325 \ \lambda \ 316 \ nm \atop 1 \ 262 \ \ \ \ 272 \ nm$ pH 7

EXAMPLE 12

N-[2-[4-(N$^\alpha$,N$^\omega$-Diacetyl-DL-lysylamino)phenyl]-4-hydroxy-5-pyrimidinylcarbonyl]-7-[D-2-amino-2-phenylacetamido]-3-acetoxymethyl-3-cephem-4carboxylic acid A suspension of 3.8 g (9.4 mmol) of cephaloglycin, 4.0 g (8.1 mmol) of 2-[4-(N$^\alpha$,N$^\omega$-diacetyl-DL-lysylamino)phenyl]-4-hydroxy-5-pyrimidine carboxylic acid imidazolide, and 75 ml of N,N-dimethylacetamide is stirred at room temperature for 4 hrs and filtered. The filtrate is poured onto 300 g of ice water, stirred for 30 min, acidified to pH 2.0 with dilute hydrochloric acid, and stirred for 30 min. The precipitated acid is filtered and washed with water, resuspended in 100 ml of ice water and dissolved by adjusting the pH to 6.5 with 0.1 N sodium hydroxide. The solution is clarified by filtration and lyophilized to give 5.3 g of the sodium salt of the title cephalosporin derivative; $[\alpha]_D^{23} + 23.8°$ (cl, pH 7).

$E_1^1 \ 295 \ \lambda \ 317 \ nm \atop 1 \ 238 \ \ \ \ 273 \ nm$ pH 7

EXAMPLE 13

N-[2-[4-(N-Acetyl-DL-prolylamino)phenyl]-4-hydroxy-5-pyrimidinylcarbonyl]-7-[D-2-amino-2-phenylacetamido]-3-acetoxy-methyl-3-cephem-4-carboxylic acid A suspension of 3.23 g (7.9 mmol) of cephaloglycin, 35 ml of N,N-dimethylacetamide, and 3.05 g (7.25 mmol) of 2-[4-(N-acetyl-DL-prolylamino)phenyl]-4-hydroxy-5-pyrimidine carboxylic acid imidazolide is stirred at room temperature and 1.05 ml (7.5 mmol) of triethylamine is added. The reaction is stirred at room temperature for 2 hrs. and filtered. After 1 hr. the filtrate is poured into 200 ml of ice water containing 7 ml of 1 N hydrochloric acid. The pH is adjusted to 3.0 with 1 N hydrochloric acid and the solid filtered. The solid is suspended in water, filtered, resuspended in water, and the pH adjusted to 6.5 with 1 N sodium hydroxide. The solution is clarified by filtration and the filtrate lyophilized to give 4.0 g of the sodium salt of the title cephalosporin derivative; $[\alpha]_D^{23} +16°$ (cl, 75% DMF/pyridine).

$$E_{1\ 253}^{1\ 326} \ \lambda \ _{272\ nm}^{316\ nm} \ pH\ 7$$

EXAMPLE 14

N-[2-[4-(N-Acetyl-DL-glutaminylamino)phenyl]-4-hydroxy-5-pyrimidinylcarbonyl]-7-[D-2-amino-2phenylacetamido]-3-acetoxymethyl-3-cephem-4-carboxylic acid Using the method of Example 13, 2.6 g (6.3 mmol) of cephaloglycin, 2.34 g (5.23 mmol) of 2-[4-(N-acetyl-DL-glutaminylamino)phenyl]-4-hydroxy-5-pyrimdine carboxylic acid imidazolide, 0.7 ml (5 mmol) of triethylamine, and 40 ml of N,N-dimethylacetamide are allowed to react at room temperature for 5 hrs. Work up and lyophilization of a pH 6.0 solution affords 1.81 g of the sodium salt of the above named cephalosporin derivative; $[\alpha]_D^{23} +28.4°$ (cl, pH 7).

$$E_{1\ 265}^{1\ 348} \ \lambda \ _{265\ nm}^{317\ nm} \ pH\ 7$$

EXAMPLE 15

N-[2-[4-(N-Acetyl-L-hydroxyprolylamino)phenyl]-4-hydroxy-5-pyrimidinylcarbonyl]-7-[D-2-amino-2-phenylacetamido]-3-acetoxymethyl-3-cephem-4-carboxylic acid A mixture of 2.16 g (5.25 mmol) of cephaloglycin, 2.31 g (4.8 mmol of 2-[4-(N-acetyl-L-hydroxyprolylamino)phenyl]-4-hydroxy-5-pyrimidine carboxylic acid N-hydroxysuccinimide ester, and 20 ml of N,N-dimethylacetamide is stirred at 0° to 5°, and 0.67 ml (4.8 mmol) of triethylamine is added. The reaction is stirred for 2 hrs and at room temperature for 2 hrs. The resulting suspension is filtered and the filtrate added to 700 ml of stirring ethyl acetate. The precipitated solid is filtered washed with ether, dried, and dissolved in 100 ml of ice water. The pH is adjusted to 2.7 with 1 N hydrochloric acid and the acid is filtered, suspended in water, and refiltered. The solid is suspended in 100 ml of ice water and dissolved by adjusting the pH to 6.5 with 1 N sodium hydroxide. The solution is clarified by filtration and the filtrate lyophilized to give 1.8 g of the sodium salt of the above named cephalosporin derivative; $[\alpha]_D^{23} +17°$ (cl, pH 7).

$$E_{1\ 256}^{1\ 232} \ \lambda \ _{274\ nm}^{317\ nm} \ pH\ 7$$

EXAMPLE 16

N-[2-[4-(N-Acetyl-γ-aminobutyrylamino)phenyl]-4-hydroxy-5-pyrimidinylcarbonyl]-7-[D-2-amino-2-phenylacetamido]-3-acetoxy-methyl-3-cephem-4-carboxylic acid A mixture of 2.7 g (6.6 mmol) of cephaloglycin, 2.5 g (6 mmol) of 2-[4-(N-acetyl-γ-aminobutyrylamino)-phenyl]-4-hydroxy-5-pyrimidine carboxylic acid imidazolide, and 30 ml of N,N-dimethylacetamide is stirred at 0° to 5° and 0.84 ml (6 mmol) of triethylamine is added. Stirring is continued at 0°-5° for 1 hr. and then at room temperature for 3 hrs. The thin suspension is filtered and the filtrate is added dropwise to 600 ml of stirring ethyl acetate. The precipitate is filtered, washed with ether, dried, and added to 200 ml of ice water. The pH is adjusted to 8.2 with 1 N sodium hydroxide and the mixture filtered. The filtrate is acidified to pH 2.0 with 1 N hydrochloric acid and the acid filtered and washed with water. The solid is resuspended in 200 ml of ice water and the pH adjusted to 7.5 with 1N sodium hydroxide. Filtration and lyophilization gives 3.01 g of the sodium salt of the title cephalosporin; $[\alpha]_D^{23} +40°$ (cl, pH 7).

$$E_{1\ 239}^{1\ 332} \ \lambda \ _{273\ nm}^{318\ nm} \ pH\ 7$$

EXAMPLE 17

N-[2-[4-(N-Acetyl-D-valylamino)phenyl]-4-hydroxy-5-pyrimidinylcarbonyl]-7-[D-2-amino-2-phenylacetamido]-3-acetoxymethyl-3-cephem-4-carboxylic acid A suspension of 2.87 g (7 mmol) of cephaloglycin and 20 ml of N,N-dimethylacetamide is stirred at 0° to 5° and 2.64 g (6.26 mmol) of 2-[4-(N-acetyl-D-valylamino)phenyl]-4-hydroxy-5-pyrimidine carboxylic acid imidazolide is added followed by 0.84 ml (6 mmol) of triethylamine. The mixture is stirred at 0° to 5° C. for 3 hrs and then allowed to stand at room temperature overnight. The mixture is filtered and the filtrate added to 200 ml of stirring ethyl acetate. The pH is adjusted to 2.5 with 1 N hydrochloric acid and the solid acid filtered, washed with ice water, and resuspended in 50 ml of water. The pH is brought to 6.5 with 1 N sodium hydroxide and the solution lyophilized to give 3.35 g of the sodium salt of the title compound; $[\alpha]_D^{23} +47.5°$ (cl, pH 7).

$$E_{1\ 251}^{1\ 321} \ \lambda \ _{272\ nm}^{318\ nm} \ pH\ 7$$

EXAMPLE 18

N-[2-[4-(D-Alanylamino)phenyl]-4-hydroxy-5-pyrimidinylcarbonyl]-7-[D-2-amino-2-phenylacetamido]-3-acetoxymethyl-3cephem-4-carboxylic acid A suspension of 3.8 g (8.4 mmol) of 2-[4-(N-t-butoxycarbonyl-D-alanylamino)phenyl]-4-hydroxy-5-pyrimidine carboxylic acid imidazolide and 40 ml of N,N-dimethylacetamide is stirred at room temperature and 3.54 g (9.0 mmol) of cephaloglycin is added. The reaction mixture is stirred at room temperature for 4.5 hrs and 3 ml (9.9 mmol) of 3.3 M sodium 2-ethyl-hexanoate in N,N-dimethylacetamide is added. The reaction is filtered and the filtrate is added to 200 ml of well stirred ethyl acetate and the precipitated solid is filtered, washed with 1:1 ethyl acetate ether, ether and dried. The dry powder is dissolved in water and the pH adjusted to 2.3 with 1 N hydrochloric acid. The solid acid is filtered, washed with water, suspended in 100 ml of water and lyophilized to give 5.5 g of N-[2-[4-(N-t-butoxycarbonyl-D-alanylamino)phenyl]-4-hydroxy-5-pyrimidinylcarbonyl]-7-[D-2-amino-2-phenylacetamido]-3-acetoxymethyl-3-cephem-4-carboxylic acid; $[\alpha]_D^{23}+61°$ (c0.84, 20% methanol/pH 7).

A solution of 20 ml of trifluoroacetic acid and 2 ml of anisole is stirred at 5° and 2.4 g (3.0 mmol) of the above protected cephalosporin is added in small portions. The mixture is stirred at 5° for 1.5 hrs, filtered, and the filtrate evaporated under vacuum. The residue is added to 150 ml of well stirred ether and the precipitate is allowed to stir for 30 minutes, filtered, washed with ether, and dried. The solid is suspended in water at 5° and the pH adjusted to 4.5 with 1 N sodium hydroxide. The precipitate is filtered and washed with ice cold water, resuspended in water at 5° and the pH is readjusted to 4.5. The solid is filtered washed with water, resuspended in water and lyophilized to give 1.5 g of solid. A 0.75 g portion is suspended in 100 ml of ice cold water and the pH adjusted to 8.4 with 1 N sodium hydroxide. The solution is clarified by filtration and lyophilized to give 1.2 g of the sodium salt of the title cephalosporin derivative; $[\alpha]_D^{23}+37.2°$ (c1, 50% methanol/pH 7).

$$E_1^1 \begin{smallmatrix} 306 \\ 231 \end{smallmatrix} \lambda \begin{smallmatrix} 317 \text{ nm} \\ 276 \text{ nm} \end{smallmatrix} \text{pH 7}$$

EXAMPLE 19

N-[2-[4-(N-Acetyl-D-alanylamino)phenyl]-4-hydroxy-5-pyrimidinylcarbonyl]-7-[D-2-amino-2-(2-thienyl)acetamido]-3-acetoxymethyl-3-cephem-4-carboxylic acid A solution of 1.87 g (3.56 mmol) of 7-[D-2-amino-2-(2-thienyl)acetamido]-3-acetyloxy-3-cephem-4-carboxylic acid trifluoracetic acid salt [U.S. Pat. No. 3,311,621], 1.30 g (3.3 mmol) of 2-[4-(N-acetyl-D-alanylamino)phenyl]-4-hydroxy-5-pyrimidine carboxylic acid imidazolide, and 12 ml of N,N-dimethylacetamide is stirred at room temperature and 0.5 ml (3.6 mmol) of triethylamine is added. The reaction mixture is stirred at room temperature for 2.5 hrs and 0.5 ml (3.6 mmol) of triethylamine is added and the solution is added dropwise to 100 ml of rapidly stirred ethyl acetate. The precipitated salt is filtered, washed with ether and ethyl acetate, and dried. The solid is dissolved in 100 ml of water and clarified by filtration. The filtrate is cooled with an ice bath and the pH adjusted to 2.3 with 1 N hydrochloric acid. The solid acid is filtered, washed with water, suspended in 100 ml of water with ice bath cooling and dissolved by adjusting to pH 7.1 with 1 N sodium hydroxide. Filtration followed by lyophilization of the filtrate gives 2.56 g of the sodium salt of the title cephalosporin; $[\alpha]_D^{23}+60.6°$ (c1, pH 7).

$$E_1^1 \begin{smallmatrix} 284 \\ 227 \end{smallmatrix} \lambda \begin{smallmatrix} 317 \text{ nm} \\ 272 \text{ nm} \end{smallmatrix} \text{pH 7}$$

EXAMPLE 20

N-[2-[4-(N-Acetyl-DL-alanylamino)phenyl]-4-hydroxy-5-pyrimidinylcarbonyl]-7-[D-2-amino-2-phenylacetamido]-3-carbamoyloxymethyl-3-cephem-4-carboxylic acid A mixture of 1.78 g (3.42 mmol) of 7-[D-2-amino-2-phenylacetamido-3-carbamoyloxymethyl-3-cephem-4-carboxylic acid trifluoroacetic acid salt [Belgian Pat. No. 835238], 1.40 g (3.55 mmol) of 2-[4-(N-acethyl-DL-alanylamino)phenyl]-4hydroxy-5-pyrimidine carboxylic acid imidazolide, 2.1 ml (6.9 mmol) of 3.3 M sodium 2-ethylhexanoate in N,N-dimethylacetamide, and 15 ml of N,N-dimethylacetamide is stirred at room temperature for 3.5 hrs. The reaction mixture is added to 150 ml of ethyl acetate and the precipitate filtered, washed with ethyl acetate and dried. The crude product is dissolved in water and the pH adjusted to 2.5 with 1 N hydrochloric acid. The solid acid is filtered, resuspended in 150 ml of water and dissolved by adjusting the pH to 7.5-8.0 with 1 N sodium hydroxide. The solution is lyophilized to give 2.5 g of the sodium salt of the title cephalosporin; $[\alpha]_D^{23}+28.4°$ (c1, pH 7).

$$E_1^1 \begin{smallmatrix} 321 \\ 238 \end{smallmatrix} \lambda \begin{smallmatrix} 316 \text{ nm} \\ 275 \text{ nm} \end{smallmatrix} \text{pH 7}$$

EXAMPLE 21

N-[2-[4-(N-Acetyl-D-alanylamino)phenyl]-4-hydroxy-5-pyrimidinylcarbonyl]-7-[D-2-amino-2-phenylacetamido-3-carbamoyloxymethyl-3-cephem-4-carboxylic acid Using the method of Example 20, 1.50 g (2.88 mmol) of 7-[D-2-amino-2-phenylacetamido]-3-carbamoyloxymethyl-3-cephem-4-carboxylic acid trifluoroacetic acid salt [Belgium Pat. No. 835238], 1.13 g (2.87 mmol) of 2-[4-(N-acetyl-D-alanylamino)-phenyl]-4-hydroxy-5-pyrimidine carboxylic acid imidazolide, 1.77 ml (5.84 mmol) of 3.3 M sodium 2-ethylhexanoate in N,N-dimethylacetamide, and 10 ml of N,N-dimethylacetamide are allowed to react for 1.5 hrs. Work up gives 1.8 g of the sodium salt of the title cephalosporin; $[\alpha]_D^{23}+98°$ (c1, pH 8.3).

$$E_1^1 \begin{smallmatrix} 317 \\ 251 \end{smallmatrix} \lambda \begin{smallmatrix} 316 \text{ nm} \\ 271 \text{ nm} \end{smallmatrix} \text{pH 7}$$

EXAMPLE 22

N-[2-[4-(N-Acetylglycylamino)phenyl]-4-hydroxy-5-pyrimidinylcarbonyl]-7-[D-2-amino-2-phenylacetamidol-3-[[(1-methyl-1H-tetrazol-5-yl)thio]-methyl]-3-cephem-4-carboxylic acid A mixture of 4.62 g (10 mmol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 3.8 g (10 mmol) of 2-[4-acetylglycylamino)-phenyl]-4-hydroxy-5-pyrimidine carboxylic acid imidazolide, and 50 ml of N,N-dimethylacetamide is stirred at 0°-5° and a solution of 1.4 ml (10 mmol) of triethylamine in 10 ml of N,N-dimethylacetamide is added dropwise. The reaction mixture is stirred at 0°-5° for 2 hrs and the resulting solution is poured into 400 ml of cold water. The pH is adjusted to 2.0 with 1 N hydrochloric acid and the precipitate filtered, washed with water and slurried in 120 ml of water. The pH is brought to 7.5 with 1 N sodium hydroxide. Insolubles are removed by filtration and the filtrate lyophilized to give 4.1 g of the sodium salt of the title compound; $[\alpha]_D^{23} +18°$ (cl, pH 7)

$$E_{1\ 260}^{1\ 308}\ \lambda\ _{279\ nm}^{319\ nm}\ \text{pH 7}$$

EXAMPLE 23

N-[2-[4-(N-Acetyl-DL-glutaminylamino)phenyl]-4-hydroxy-5-pyrimidinylcarbonyl]-7-[D-2-amino-2-phenylacetamido]-3-[[1-methyl-1H-tetrazol-5-yl)thio]-methyl]-3-cephem-4-carboxylic acid A mixture of 1.90 g (4 mmol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 1.79 g (4 mmol) of 2-[4-(N-acetyl-DL-glutaminylamino)phenyl]-4-hydroxy-5-pyrimidine carboxylic acid imidazolide, and 70 ml of N,N-dimethylacetamide is stirred at room temperature for 3 hrs and 1.2 ml (4 mmol) 3.3 M sodium 2-ethylhexanoate in N,N-dimethylacetamide is added. The resulting solution is poured into 300 ml of ethyl acetate and the precipitate is collected, washed with ethyl acetate, and dissolved in 250 ml of cold water. The pH is adjusted to 2.3 with 1 N hydrochloric acid and the free acid filtered and resuspended in 120 ml of cold water and the pH adjusted to 7.5 with 1 N sodium hydroxide. Filtration and lyophilization of the filtrate gives 2.0 g of the sodium salt of the title cephalosporin; $[\alpha]_D^{23}+ -4°$ (cl, pH 7).

$$E_{1\ 258}^{1\ 311}\ \lambda\ _{276\ nm}^{316\ nm}\ \text{pH 7}$$

EXAMPLE 24

N-[2-[4-(N-Acetyl-DL-alanylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid A mixture of 2.82 g (6 mmol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 2.4 g (6 mmol) of 2-[4-N-acetyl-DL-alanylamino)phenyl]-4-hydroxy-5-pyrimidine carboxylic acid imidazolide, and 25 ml of N,N-dimethylacetamide is stirred at room temperature and 1.82 ml (6 mmol) of 3.3 M sodium 2-ethylhexanoate in N,N-dimethylacetamide is added. The reaction mixture is stirred at room temperature for 3 hrs and filtered. The filtrate is poured into 300 ml of stirring ethyl acetate and the precipitate is collected, washed with ethyl acetate and dried to give 4.45 g of the sodium salt of the title cephalosporin; $[\alpha]_D^{23} -9.8°$ (cl, pH 7).

$$E_{1\ 267}^{1\ 284}\ \lambda\ _{277\ nm}^{316\ nm}\ \text{pH 7}$$

EXAMPLE 25

N-[2-[4-(N-Acetyl-D-alanylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid A mixture of 2.82 g (6 mmol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 2.4 g (6 mmol) of 2-[4-(N-acetyl-D-alanylamino)phenyl]-4-hydroxy-5-pyrimidine carboxylic acid imidazolide, and 25 ml of N,N-dimethylacetamide is stirred at room temperature for 3 hrs and 1.82 ml (6 mmol) of 3.3 M sodium 2-ethylhexanoate in N,N-dimethylacetamide is added. The solution is then poured into 300 ml of ethyl acetate with stirring. The precipitated solids are collected, washed with ethyl acetate and dried to give 5.2 g of the sodium salt of the title cephalosporin; $[\alpha]_D^{23}+27.4°$ (cl, pH 7).

$$E_{1\ 265}^{1\ 292}\ \lambda\ _{275\ nm}^{315\ nm}\ \text{pH 7}$$

EXAMPLE 26

N-[2-[4-(N-Acetyl-L-alanylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid Using the method of Example 25, 2.82 g (6 mmol) of 7-[D-2-amino-2-phenylacetamido]-3-[[(1-methyl-1H-tetrazol-5-yl)-thio)methyl]-3-cephem-4-carboxylic acid [J. Antibiot., 29, 65 (1976)] and 2.4 g (6 mmol) of 2-[4-(N-acetyl-L-alanylamino)-phenyl]-4-hydroxy-5-pyrimidine carboxylic acid imidazolide are allowed to react in 25 ml of N,N-dimethylacetamide at room temperature for 3 hrs. Work up with 1.82 ml (6 mmol) of 3.3 M sodium 2-ethylhexanoate in N,N-dimethylacetamide affords 5.1 g of the sodium salt of the title cephalosporin; $[\alpha]_D^{23}-47.5°$ (cl, pH 7).

$$E_{1\ 258}^{1\ 285}\ \lambda\ _{278\ nm}^{317\ nm}\ \text{pH 7}$$

EXAMPLE 27

N-[2-[4-(N-Acetyl-aminobutyrylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid A suspension of 3.2 g (6 mmol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 3.2 g (6 mmol) of 2-[4-(N-acetyl-aminobutyrylamino)phenyl]-4-hydroxy-5-pyrimidine carboxylic acid imidazolide and 25 ml of N,N-dimethylacetamide is stirred at room temperature for 4 hrs and then is allowed to stand at 5° overnight. The reaction mixture is filtered and 2 ml (6.6 mmol) of 3.3 M sodium 2-ethylhexanoate in N,N-dimethylacetamide is added to the filtrate. The resulting solution is poured in a thin stream into 300 ml of ethyl acetate with stirring. The precipitated solid is collected, washed with ethyl acetate, and dried. The product is slurried in 400 ml of cold water and the pH is brought to 8 with 1 N sodium hydroxide and insoluble material is filtered off. The filtrate is acidified to pH 2 with 1 N hydrochloric acid and the precipitated solid is filtered washed with water and resuspended in 300 ml of ice water. The pH is adjusted to 7.8 with 1 N potassium hydroxide and insolubles are removed by filtration. The filtrate is lyophilized to give 2.65 g of the potassium salt of the title cephalosporin; $[\alpha]_D^{23}-31°$ (cl, MeOH/H2O, 9:1).

$E_1^1$ 281 λ 318 nm pH 7
$E_1^1$ 234   277 nm

EXAMPLE 28

N-[2-[4-N-Acetyl-alpha-aminoisobutyrylamino)-phenyl]-4-hydroxy-5-pyrimidinylcarbonyl]-7-[D-2-amino-2-phenylacetamido]-3-[[(1-methyl-1H-tetrazol-5-yl)thio]methyl]-3-cephem-4-carboxylic acid A suspension of 3.1 g (6.7 mmol) of 7-[D-amino-2-phenylacetamido]-3-[[(1-methyl-1H-tetrazol-5-yl)methyl]-3-cephem-4-carboxylic acid [J. Antibiot., 29, 65 (1976), 2.72 g (6.6 mmol) of 2-[4-(N-acetyl-alpha-aminoisobutyrylamino)phenyl]-4-hydroxy-5-pyrimidine carboxylic acid imidazolide and 25 ml of N,N-dimethylacetamide is stirred at room temperature for 4 hrs. A trace of insoluble material is filtered and 2.1 ml (7 mmol) of 3.3 M sodium 2-ethylhexanoate is added to the filtrate. The filtrate is poured in a thin stream into 300 ml of stirring ethyl acetate. The precipitated sodium salt is filtered, washed with ethyl acetate, and dried. The solid is dissolved in 300 ml of water at 0° to 5° and the pH is adjusted to 2.5 with 1 N hydrochloric acid. The precipitated acid is collected with the help of an inert filer aid and the filter cake is then slurried in 150 ml of ice water and the pH is adjusted to 6.8 with 1 N sodium hydroxide. The insoluble material is removed by filtration and the filtrate lyophilized to give 4.73 g of the sodium salt of the title cephalosporin derivative; $[\alpha]_D^{23°}$ (c1, pH 7).

$E_1^1$ 269 λ 316 nm pH 7
$E_1^1$ 250   275 nm

EXAMPLE 29

N-[2-[4-N-Acetyl-D-valylamino)phenyl]-4-hydroxy-5-pyrmidinylcarbonyl]-7-[D-2-amino-2-phenylacetamido]-3-[[(1-methyl-1H-tetrazol-5-yl)thio]-methyl]-3-cephem-4-carboxylic acid A mixture of 2.6 g (5 mmol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 1.9 g (4.5 mmol) of 2-[4-(N-acetyl-D-valylamino)phenyl]-4-hydroxy-5-pyrimidine carboxylic acid imidazolide, and 40 ml of N,N-dimethylacetamide is stirred at room temperature for 1 hr. The reaction mixture is filtered and the filtrate cooled in an ice bath and 1.5 ml (5 mmol) of 3.3 M sodium 2-ethylhexanoate in N,N-dimethylacetamide is added. The resulting solution is added dropwise to 600 ml of stirring ethyl acetate and the precipitate filtered. The solid is suspended in a solution of 300 ml of ethyl acetate and 200 ml of ether for 20 min and filtered again and dried. The solid is dissolved in 200 ml of ice water and the pH taken to 2.5 with 1 N hydrochloric acid. The precipitated acid is collected and resuspended in 100 ml of water. The pH is adjusted to 6.5 with 1 N sodium hydroxide and the resulting solution is lyophilized to give 2.8 g of crude sodium salt. The compound is dissolved in 15 ml of water and acetone is added to the cloud point. The mixture is filtered and the filtrate is treated with more acetone and the solids filtered. Additional acetone is added to the filtrate and another crop of solids is obtained. These latter two fractions are combined and lyophilized to give 1.4 g of the sodium salt of the title cephalosporin derivative; $[\alpha]_D^{23}$ −1.2° (c1, pH 7).

$E_1^1$ 258 λ 317 nm pH 7
$E_1^1$ 240   275 nm

N-[2[4-(N-Acetyl-L-hydroxyprolylamino)phenyl]-4-hydroxy-5-pyrimidinylcarbonyl]-7-[D-2-amino2-phenylacetamido]-3-[[(1-methyl-1H-tetrazol-5-yl)thio]-methyl]-3-cephem-4-carboxylic acid A mixture of 3.43 g (6.6 mmol) of 7-[D-2-amino-2-phenylacetmido]-3-[[(1-methyl-1H-tetrazol-5-yl)thio]-methyl]-3-cephem-4-carboxylic acid [J. Antibiot., 29, 65 (1976)] 2.9 g (6 mmol) of 2-[4-(N-acetyl-L-hydroxy-prolylamino)phenyl]-4-hydroxy-5-pyrimidine carboxylic acid N-hydroxy succinimide ester, and 30 ml of N,N-dimethylacetamide is stirred at 0°–5° for 1 hr and then at room temperature for 4 hrs. The reaction is fitered an 1.8 ml (6 mmol) of 3.3 M sodium 2-ethylhexanoate in N,N-dimethylacetamide is added. The resulting solution is added dropwise to 700 ml of stirring ethyl acetate and the precipitated solids filtered, resuspended in 500 ml of ethyl acetate and filtered again and dried. The crude sodium salt is dissolved in water and the solution is acidified to pH 2.5 with 1N hydrochloric acid. The precipitated acid is collected by filtration, suspended in 100 ml of ice water and dissolved by adjusting the pH to 6.5 with 1N sodium hydroxide. The solution is lyophilized to give 3.7 g of the sodium salt of the title cephalosporin; $[\alpha]_D^{23}$ −29.6° (c1, pH 7).

$E_1^1$ 277 λ 317 nm pH 7
$E_1^1$ 263   276 nm

N-[2[4-(N-Acetyl-D-alanylamino)phenyl]-4-hydroxy-5-pyrimidinyl-carbonyl]-7-[D-2-amino-2-(4-hydroxyphenyl)acetamido]-3-[[(1-methyl-1H-tetrazol-5-yl)thiol]methyl]-3-cephem-4-carboxylic acid A mixture of 2.36 g (4.95 mmol) of 7-[D-2-amino-2-(4-hydroxyphenyl)acetamido]-3-[[(1-methyl-1Htetrazol-5-yl)thio]methyl]-3-cephem-4-carboxylic acid [J. Antibiot., 29, 65 (1976)], 1.90 g (4.82 mmol) of 2-[4-(N-acetyl-D-alanylamino)phenyl)]-4-hydroxy-5-pyrimidine carboxylic acid imidazolide, and 20 ml of N,N-dimehtylacetamide is stirred at room temperature for 2.5 hrs. and 2 ml (6.6 mmol) of sodium 2-ethylhexanoate in N,N-dimethylacetamide is added. The resulting solution is added dropwise to 200 ml of stirring ethyl acetate and the precipitate filtered, washed with ethyl acetate, and dried. The solids are dissolved in water and the pH adjusted to 2 with 1N hydrochloric acid and the precipitated acid filtered, washed with ice water, resuspended in 150 ml of ice water and dissolved by adjusting the pH to 7.6 with 1N sodium hydroxide. Lyophilization gives 3.6 g of the sodium salt of the title cephalosporin; $[\alpha]_D^{23}$ +35° (c0.85, pH 8.2)

$E_1^1$ 316 λ 316 nm pH 7
$E_1^1$ 286   275

EXAMPLE 32

N-[2-[4-(N-Acetyl-DL-alanylamino)phenyl]-4-hydroxy-5-pyrimidinylcarbonyl]-7-[D-2-amino-2-(4-hydroxyphenyl)acetamido]-3-[[(1-methyl-1H-tetrazol-5-yl)thio]methyl]-3-cephem-4-carboxylic acid A solution of 2.0 (4.19 mmol) of 7-[D-2-amino-2-(4-hydroxyphenyl)acetamido]-3-[[(1-methyl-1H-tetrazol-5-yl)thio]methyl]-3-cephem-4-carboxylic acid [J. Antibiot., 29., 65 (1976)] and 20 ml of N,N-dimethylacetamide is stirred with ice bath cooling and 1.5 g (3.81 mmol) of 2-[4-(N-acetyl-DL-alanylamino)phenyl]-4-hydroxy-5-pyrimidine carboxylic acid imidazolide is added. The ice bath is removed and the reaction is stirred at room temperature for 3.5 hrs and 2.0 ml (6.5 mmol) of 3.27 M sodium 2-ethylhexanoate in N,N-dimethylacetamide is added. The solution is added dropwise to 200 ml of ethyl acetate and the precipitate filtered, washed with ethyl acetate, and dried. The solid is dissolved in 100 ml of water at 0°–5° C. and the pH adjusted to 2.3 with 1 N hydrochloric acid. The precipitated acid is filtered, washed with water, resuspended in ice water and dissolved by adjusting the pH to 7.4 with 1 N sodium hydroxide. The solution is clarified by filtration and lyophilized to give 3.8 g of the sodium salt of the title cephalosporin; $[\alpha]_D^{23} -21°$ (cl, pH 7).

$$E_1^1 \; {296 \atop 276} \; \lambda \; {316 \text{ nm} \atop 275 \text{ nm}} \; pH \; 7$$

EXAMPLE 33

N-[2-[4-(N-Acetyl-L-alanylamino)phenyl]-4-hydroxy-5-pyrimidinylcarbonyl]-7-[D-2-amino-2-phenylacetamido]-3-[[(1[carboxymethyl-1H-tetrazol-5-yl)thio]methyl]-3-cephem-4-carboxylic acid A suspension of 5 g (8 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 30 ml of N,N-dimethylacetamide is stirred at 0°–5° and 2.3 ml (16 mmol) of triethylamine is added dropwise followed by 3.15 g (8 mmol) of 2-[4[(N-acetyl-L-alanylamino)phenyl]-4-hydroxy-5-pyrimidine carboxylic acid imidazolide. The reaction solution is stirred at 0°–5° for 1 hr and at room temperature for 3 hrs and 7.6 ml (25 mmol) of 3.3 M sodium 2-ethylhexanoate in N,N-dimethylacetamide is added. The solution is poured in a thin stream into 350 ml of rapidly stirred ethyl acetate and the precipitate filtered, washed with ethyl acetate and dried. The crude salt is purified by dissolving in 30 ml of water and putting the solution on a column containing 600 ml of Sephadex G-10 and eluting with degassed water. Factions containing the desired product as determined by thin layer chromatography are combined and lyophilized to give 3.25 g of the disodium salt of the title compound; $[\alpha]_D^{23} -21.5°$ (cl, pH 7).

$$E_1^1 \; {264 \atop 244} \; \lambda \; {316 \text{ nm} \atop 276 \text{ nm}} \; pH \; 7$$

EXAMPLE 34

N-[2-[4-(N-Acetyl-D-alanylamino)phenyl]-4-hydroxy-5-pyrimidinylcarbonyl]-7-[D-2-amino-2-phenylacetamido]-3-[[(1-carboxymethyl-1H-tetrazol-5-yl)thio]methyl]-3-cephem-4-carboxylic acid A suspension of 3.72 g (6 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 30 ml of N,N-dimethylacetamide is stirred at 0°–5° C. and 1.7 ml (12 mmol) of triethylamine followed by 2.17 g (5.5 m mol) of 2-[4-(N-acetyl-D-alanylamino)phenyl]-4-hydroxy-5-pyrimidine carboxylic acid imidazolide is added. The mixture is stirred at room temperature for 3 hrs and 0.84 ml (6 mmol) of triethylamine is added and the solution is poured in a thin stream into 300 ml of stirring ethyl acetate. The precipitated salt is collected washed with ethyl acetate and dried. The solid is dissolved in 300 ml of water at 0°–5° C. and the pH is adjusted to 2.2 with 1 N hydrochloric acid. The precipitated solids are filtered washed with 0.01 N hydrochloric acid, and suspended in 200 ml of ice water and dissolved by adjusting the pH to 7.2 with 1 N sodium hydroxide. The solution is clarified by filtration and lyophilized to give 4.3 g of the disodium salt of the title cephalosporin; $[\alpha]_D^{23} \pm 22.6°$ (cl, pH 7).

$$E_1^1 \; {339 \atop 225} \; \lambda \; {316 \text{ nm} \atop 276 \text{ nm}} \; pH \; 7$$

EXAMPLE 35

N-[2-[4-(N-Acetyl-DL-alanylamino)phenyl]-4-hydroxy-5-pyrimidinylcarbonyl]-7-[D-2-phenylacetamido-3-[[(1-carboxymethyl-1H-tetrazol-5-yl)thio]methyl]-3-cephem-4-carboxylic acid A suspension of 3.3 g (5.3 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 20 ml of dry N,N-dimethylacetamide is stirred at 0°–5° C. and 1.5 ml (10.6 mmol) of triethylamine is added dropwise followed by 2 g (5 mmol) of (2-[4-(N-acetyl-DL-alanylamino)phenyl]-4-hydroxy-5-pyrimidine carboxylic acid imidazolide. The mixture is stirred at room temperature for 5 hrs and 6.1 ml (20 mmol) of 3.27 M sodium 2-ethylhexanoate is added and the solution is poured in a thin stream into 300 ml of stirring ethyl acetate. The precipitate is filtered, washed with ethyl acetate, and dried. The solid is dissolved in 80 ml of cold water, the pH is adjusted to 7.0 with 1 N hydrochloric acid and the solution is put on a column of 450 ml of Sephadex G-10 and the column is eluted with degassed water. Fractions containing the desired product as determined by thin layer chromatography are combined and the pH 6.7 solution lyophilized to give 2.9 g of the disodium salt of the title cephalosporin; $[\alpha]_D^{23} +8.4°$ (cl, pH 7).

$$E_1^1 \; {228 \atop 218} \; \lambda \; {316 \text{ nm} \atop 276 \text{ nm}} \; pH \; 7$$

EXAMPLE 36

N-[2-[4-(N-Acetyl-L-hydroxyprolylamino)phenyl]-4-hydroxy-5-pyrimidinylcarbonyl]-7-[D-2-amino-2-phenylacetamido]-3-[[(1-carboxymethyl-1H-tetrazol-5-yl)thio]methyl]-3-cephem-4-carboxylic acid A solution of 3.71 g (6 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 25 ml of N,N-dimethylacetamide is stirred at room temperature and 2.90 g (6 mmol) of 2-[4-(N-acetyl-L-hydroxyprolylamino)phenyl]-4-hydroxy-5-pyrimidine carboxylic acid N-hydroxy succinimide ester is added followed by 1.25 ml (9 mmol) of triethylamine. The resulting solution is stirred at room temperature for 4.5 hrs and 1.25 ml (9 mmol) of triethylamine is added and the solution poured into 300 ml of rapidly stirred ethyl acetate. The precipitated solid is filtered washed with ethyl acetate and ether and dried. The salt is dissolved in 250 ml of ice water and acidified to pH 2 with 1 N hydrochloric acid. The acid is filtered, resuspended in 100 ml of 0.01 N hydrochloric acid, the pH adjusted to 2.2, and the solids filtered. The solid is suspended in water and dissolved by adjusting the pH to 6.8 with 1 N sodium hydroxide. The solution is lyophilized to give 4.6 g of the disodium salt of the title cephalosporin derivative; $[\alpha]_D^{23} - 17.4°$ (cl, pH 7).

$$E_1^1 \; {253 \atop 233} \; \lambda \; {317 \text{ nm} \atop 277 \text{ nm}} \; \text{pH 7}$$

EXAMPLE 37

N-[2-[4-(N-Acetyl-D-alanylamino)phenyl]-4-hydroxy-5-pyrimidinylcarbonyl)-7-[D-2amino-2-(4-hydroxyphenyl)acetamido]-3-[[(1-carboxymethyl-1H-tetrazol-5-yl)thio]methyl]-3-cephem-4-carboxylic acid A solution of 2.83 g (4.46 mmol) of 7-[D-2-amino-2-(4-hydroxyphenyl)acetamido]-3-[[(1-carboxymethyl-1H-tetrazol-5-yl)thio]methyl]-3-cephem-4-carboxylic acid [Chem. Abstr., 86, 72667w (1977)] and 20 ml of N,N-dimethylacetamide is stirred at 0°–5° C. and 1.76 g (4.46 mmol) of 2-[4-(N-acetyl-D-alanylamino)phenyl]-4-hydroxy-5-pyrimidine carboxylic acid imidazolide is added followed by 0.93 ml of (6.7 mmol) of triethylamine. The solution is stirred at 0°–5° for 15 min and at room temperature for 2 hrs and 0.93 ml (6.7 mmol) of triethylamine is added. The reaction mixture is poured in a thin stream into 250 ml of stirring ethyl acetate and the precipitated solid filtered, washed with ethyl acetate and ether, and dried. The crude salt is dissolved in 200 ml of ice water and the pH adjusted to 2.1 with 1 N hydrochloric acid and the precipitated acid filtered. The solid is suspended in 75 ml of 0.01 N hydrochloric acid, the pH is adjusted to 2.2 with 1 N hydrochloric acid, and the solid filtered. The filter cake is resuspended in water and dissolved by adjusting the pH to 7.0 with 1 N sodium hydroxide. The solution is clarified by filtration and lyophilized to afford 3.19 g of the disodium salt of the title cephalosporin; $[\alpha]_D^{23} + 21.5°$ (cl, pH 7).

$$E_1^1 \; {273 \atop 258} \; \lambda \; {316 \text{ nm} \atop 273 \text{ nm}} \; \text{pH 7}$$

EXAMPLE 38

N-[2-[4-(D-Alanylamino)phenyl]-4-hydroxy-5-pyrimidinylcarbonyl]-7-[D-2-amino-2-phenylacetamido]-3-[[(1-carboxymethyl-1H-tetrazol-5-yl)thio]-methyl]-3-cephem-4-carboxylic acid A solution of 4.98 g (7 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977) and 100 ml of N,N-dimethylacetamide is stirred at room temperature and 3.0 g (6.63 mmol) of 2-[4-(N-t-butoxycarbonyl-D-alanylamino)phenyl]-4-hydroxy-5-pyrimidine carboxylic acid imidazolide is added. The resulting solution is cooled to 5° C. and 1.96 ml (14 mmol) of triethylamine is added. The reaction mixture is stirred at 5° C. for 2 hrs and at room temperature for 2 hrs and the cooled to 5° and 0.97 ml (7 mmol) of triethylamine is added. The resulting solution is added to 700 ml of rapidly stirred ethyl acetate and stirring continued for 1 hr. The precipitate is filtered washed with ethyl acetate, ether, and dried to give 4.0 g of the bis-triethylamine salt of N-[2-[4-(N-t-butoxycarbonyl-D-alanylamino)-phenyl]-4-hydroxy-5-pyrimidinylcarbonyl]-7-[D-2-amino-2-phenylacetamido]-3-[[(1-carboxymethyl-1H-tetrazol-5-yl)thio]-methyl]-3-cephem-4-carboxylic acid.

A solution of 30 ml of trifluoroacetic acid and 10 ml of anisole is stirred at 5° C. and 4.0 g (4.5 mmol) of the above protected cephalosporin salt is added and the solution stirred at 5° C. for 1 hr. The solvents are evaporated under vacuum and the residue is added to 400 ml of rapidly stirred ether and stirring continued for 30 min. The precipitate is filtered, washed with ether, resuspended in ether, stirred for 30 min and filtered, washed with ether, and dried. The solid is dissolved in 200 ml of water at 5° C. and the pH is adjusted to 2.0 with 6 N hydrochloric acid. The precipitated acid is filtered, washed with ice cold water, resuspended in 200 ml of water at 5° C., and dissolved by adjusting the pH to 6.8 with 1 N sodium hydroxide. The solution is clarified by filtration and lyophilized to give 3.2 g of the sodium salt of the title compound; $[\alpha]_D^{23} - 7.6°$ (cl, pH 7).

$$E_1^1 \; {284 \atop 265} \; \lambda \; {315 \text{ nm} \atop 275 \text{ nm}} \; \text{pH 7}$$

EXAMPLE 39

N-[2-[4-(N-Acetylglycylamino)phenyl]-4-hydroxy-5-pyrimidinylcarbonyl]-7-[D-2-amino-2-phenylacetamido]-3-[[(5-methyl-1,3,4-thiadiazol-2-yl)thio]methyl]-3-cephem-4-carboxylic acid A mixture of 2.32 g (4 mmol) of 7-[D-2-amino-2-phenylacetamido]-3-[[(5-methyl-1,3,4-thiadiazol-2-thio]methyl]-3-cephem-4-carboxylic acid trifluoroacetic acid salt [J. Antibiot., 29, 65 (1976], 1.51 g (4 mmol) of 2-[4-(N-acetylglycylamino)-phenyl]-4-hydroxy-5-pyrimidine carboxylic acid imidazolide, and 20 ml of N,N-dimethylacetamide is stirred at room temperature and 0.56 ml (4 mmol) of triethylamine is added. The reaction is stirred at room temperature for 4.5 hours and poured into 150 ml of ice water. The dark solution is clarified by filtration and the pH of the filtrate is adjusted to 2.5 with 6 N hydrochloric acid and the precipitated acid filtered. The solids are dissolved in 150 ml of water by adjusting the pH to 7.5 with 1 N sodium hydroxide. Lyophilization gives 2.05 g of solid which is combined with 0.5 g from another run redissolved in water and lyophilized to give 2.2 g of the sodium salt of the title cephalosporin; $[\alpha]_D^{23} - 87°$ (cl, pH 7).

$E_1^1 342 \lambda 315$ mm pH 7

EXAMPLE 40

N-[2-[4-(N-Acetyl-DL-alanylamino)phenyl]-4-hydroxy-5-pyrimidinylcarbonyl]-7-[D-2-amino-2-phenylacetamido]-3-[[(5-methyl-1,3,4-thiadiazoyl-2-thio]methyl]-3-cephem-4-carboxylic acid A solution of 2.90 g (5 mmol) of 7-[D-2-amino-2-phenylacetamido]-3-[[(5-methyl-1,3,4-thiadiazol-2-yl)thio]methyl]-3-cephem-4-carboxylic acid trifluoroacetic acid salt [J. Antibiot., 29, 65 (1976)] and 25 ml of N,N-dimethylacetamide is stirred at room temperature and 2.0 g (5 mmol) of 2-[4-(N-acetyl-DL-alanylamino)-phenyl]-4-hydroxy-5-pyrimidine carboxylic acid imidazolide is added followed by 0.7 ml (5 mmol) of triethylamine. The reaction mixture is stirred at room temperature for 45 min and solution is observed. Next another 0.7 ml (5 mmol) of triethylamine is added dropwise over a 45 min period and the solution is stirred for 2 hours. The reaction mixture is added to excess ethyl acetate and the precipitate filtered, washed with ethyl acetate, and dried. The solids are dissolved in 150 ml of ice water and the pH adjusted to 6.5. This solution is added to 100 ml of 0.5 M formic acid, the precipitate filtered, washed with ice water, suspended in ice water and filtered again. The solids are resuspended in 100 ml of ice water and centrifuged, decanted, and dissolved in 100 ml of ice water by adjusting the pH to 7.4 with 1 N sodium hydroxide. The solution is lyophilized to give 2.85 g of the sodium salt of the title cephalosporin; $[\alpha]_D^{23} -53.8°$ (cl, pH 7).

$$E_1^1 \begin{array}{cc} 294 \\ 274 \end{array} \lambda \begin{array}{c} 314 \text{ nm} \\ 280 \text{ nm} \end{array} \Big\} \text{ pH 7}$$

EXAMPLE 41

N-[2-[4-(L-Glutaminylamino)phenyl]-4-hydroxy-5-pyrimidinylcarbonyl]-7-[D-2-amino-2-phenylacetamido]-3-[[(1-carboxymethyl-1H-tetrazol-5-yl)thio]methyl]-3-cephem-4-carboxylic acid A solution of 1.6 g (3.1 mmol) of 2-[4-(N-t-butoxycarbonyl-L-glutaminylamino)phenyl]-4-hydroxy-5-pyrimidine carboxylic acid imidazolide, 2.1 g (3.4 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid, salt, [Chem. Abstr., 86, 189979r (1977)] and 40 ml of N,N-dimethylacetamide is stirred at 0°-5° C. and 0.69 g (6.8 mmol) of triethylamine is added over 10 min. The reaction is stirred at 5° C. for 2 hrs, allowed to come to room temperature over the next 3 hrs, and 0.35 g (3.4 mmol) of triethylamine is added. The resulting solution is added to 300 ml of rapidly stirred ethyl acetate. The precipitated solid is filtered, washed with 1:1 ethyl acetate ether, ether, and dried to give 1.2 g of the protected cephalosporin derivative.

A solution of 5 ml anisole and 15 ml of trifluoroacetic acid is stirred at 0°-5° C. and 1.2 g (1.26 mmol) of the above cephalosporin derivative is added in small portions over 25 min. The mixture is stirred at 5° C. for 1 hr and the solvent is evaporated under reduced pressure and the residue is triturated with ether until a fine powder results. The powder is filtered, washed with ether, resuspended in ether, stirred for 30 min, filtered, washed with ether and dried. The dry powder is added to ice water and the resulting precipitate removed by filtration, washed with ice water, resuspended in ice water and the pH is adjusted to 6.8 with 1 N sodium hydroxide. The resulting solution is clarified by filtration and the filtrate lyophilized to give 0.85 g of the title cephalosporin; $[\alpha]_D^{23} +25°$ (cl, pH 7).

$$E_1^1 \begin{array}{cc} 242 \\ 237 \end{array} \lambda \begin{array}{c} 318 \text{ nm} \\ 276 \end{array} \text{ pH 7}$$

EXAMPLE 42

N-[2-[4-[(2-Oxo-1-pyrrolidinyl)acetylamino]phenyl]-4-hydroxy-5-pyrimidinylcarbonyl]-7-[D-2-amino-2-phenylacetamide]-3-[[(1-carboxymethyl-1H-tetrazol-5-yl)thio[methyl]-3-cephem-4-carboxylic acid A suspension of 3.4 g (5.5 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] in 30 ml of N,N-dimethylacetamide is stirred at 0°-5° C. and 1.54 ml of (11 mmol) triethylamine is added in portions, followed by 2.03 g (5 mmol) of 2-[4-[(2-Oxo-1-pyrrolidinyl)acetylamino]phenyl]-4-hydroxy-5-pyrimidine carboxylic acid imidazolide. The mixture is stirred at 0°-5° C. for 30 min and then at room temperature for 3 hrs and 0.77 ml (5.5 mmol) of triethylamine is added. The solution is poured into 300 ml ethyl acetate and the precipitated triethylamine salt is collected, and washed with ethyl acetate. The filtercake is dissolved in 300 ml water at 0°-5° C. and the pH is brought to 2.0 with 1 N hydrochloric acid. The precipitated acid is filtered, washed with water of pH 2 and suspended in 150 ml of ice water. The pH is adjusted to 7 with 1 N sodium hydroxide solution and the solution is filtered. The filtrate is lyophilized, leaving 4.0 g of the title cephalosporin as the disodium salt; $[\alpha]_D^{23} +6.6°$ (cl, pH 7)

$$E_1^1 \begin{array}{cc} 252 \\ 233 \end{array} \lambda \begin{array}{c} 317 \text{ nm} \\ 277 \text{ nm} \end{array} \text{pH 7}$$

STARTING MATERIALS

A. 2-(4-Aminophenyl)-4-hydroxy-5-pyrimidine carboxylic acid

A solution of 14.8 g (0.642 mmol) of sodium in 750 ml of dry ethanol is stirred at 0° and 44.6 g (0.214 mmol) of 4-aminobenzamidine 2HCl [Shaw and Cooley, J. Am. Chem. Soc., 79, 3561 (1957)] is added. The mixture is stirred 5 minutes under nitrogen and 46.2 g (0.214 mmol) of diethyl ethoxymethylenemalonate is added. After stirring for 30 min, the mixture is refluxed for 4 hr and allowed to stand overnight at room temperature. The salt is filtered and washed with isopropanol. The salt is suspended in 214 ml of 2 N potassium hydroxide and stirred at 70° C. for 4 hr. After treating with a small amount of charcoal, the filtrate is added to 325 ml of 2 N HCl with stirring. The acid is filtered, washed with water, ethanol, and ether, and dried to give 50.8 g of the title compound, mp 312°-314° C. dec. The product is recrystallized from dimethylacetamide-water to give 44.5 g mp 313°-314° C. dec.

$$E_1^1 = \begin{array}{cc} 920 \\ 460 \end{array} \lambda \begin{array}{c} 331 \text{ nm} \\ 227 \end{array} \Big\} \text{ pH 7}$$

B. 2-[4-(N-Benzyloxycarbonylglyclamino)phenyl]-4-hydroxy-5-pyrimidine carboxylic acid A suspension of 9.2 g (40 mmol) of 2-(4-aminophenyl)-4-hydroxy-5-pyrimidinecarboxylic acid in 300 ml of dichloromethane is stirred at room temperature and 12.1 g (120 mmol) of triethylamine is added followed by 13.1 g (120 mmol) of trimethylsilyl chloride.

The mixture is stirred for 2 hrs at room temperature and then is added to the solution below.

A solution of 8.4 g (40 mmol) of N-benzyloxycarbonylglycine and 200 ml of dichloromethane is stirred at −20° C. and 4.1 g (40 mmol) of triethylamine is added followed by 4.3 g (40 mmol) of ethyl chloroformate. The mixture is stirred at −20° C. for 30 minutes and the above silylated product is then added as rapidly as possible maintaining the temperature at −20° C. After stirring for 2 hrs at −20° C. and 4 hrs at 5° C., the mixture is allowed to come to room temperature overnight. Methanol (50 ml) is added with stirring and the product separates as a yellow solid. The solid is filtered and washed with dichloromethane and finally ether. The solid is suspended in water, filtered, and washed with ethanol and finally ether. Drying affords 9.5 g of the title compound, mp 254°–260° C. dec. Recrystallization from aqueous dimethylformamide raises the melting point to 276°–277° C. dec.

C.
2-[4-(N-Glycylamino)phenyl]-4-hydroxy-5-pyrimidine carboxylic acid

A solution of 40 ml of 30% HBr in acetic acid is stirred at room temperature and 4.5 g (10.7 mmol) of the above N-carbobenzyloxyglycyl compound is added. After vigorous carbon dioxide evolution a copious precipitate forms. The mixture is stirred for 2 hrs at room temperature and then cooled in ice. Ethyl acetate (100 ml) is added and the solid is filtered, washed well with ethyl acetate and finally ether. The dried solid is added to 100 ml of cold water and the pH raised to 10.2 with conc ammonium hydroxide. The solution is filtered and the filtrate concentrated in vacuo. The product crystallizes as needles as the ammonia evaporates. The neutral mixture is filtered and the product washed with water, ethanol and finally ether. The dried title compound weighs 2.57 g, mp 312°–313° C. dec. The product can be readily acylated to form the N-acetyl side chain.

$E_1^1 = 788 \ \lambda 310 \ nm$ pH 7–50% MeOH

D.
2-[4-N-Acetylglycylamino)phenyl]-4-hydroxy-5-pyrimidine carboxylic acid imidazolide A suspension of 2.4 g (8 mmol) of 2-[4-(N-glycylamino)phenyl]-4-hydroxy-5-pyrimidine carboxylic acid and 20 ml of dimethylformamide is stirred at room temperature and 5.5 ml (39 mmol) of triethylamine and 2.0 ml (21 mmol) of acetic anhydride are added. After standing 2 hours at room temperature the solution is poured into 50 ml of ice water and acidified to pH 2 with HCl. The product is filtered, washed with water, ethanol and finally ether. The dried 2-[4-(N-acetylglycylamino)phenyl]-4-hydroxy-5-primidine carboxylic acid weighs 2.3 g, mp 313°–315° C. dec.

$E_1^1 = 587 \lambda 308 \ nm$ pH 7

A suspension of 1.96 g (5.5 mmol) of the above pyrimidine carboxylic acid and 30 ml of dimethylformamide is stirred and 2.0 g (12 mmol) of carbonyldiimidazole is added. The mixture is heated to 55°–60° C. for 30 minutes and stirred at room temperature for 3 hours. Acetonitrile (40 ml) is added and the solid is filtered, washed with acetonitrile and ether to give 2.02 g of the title imidazolide.

E. 2-[4-(N-Acetyl-L-alanylamino)phenyl]-4-hydroxy-5-pyrimidine carboxylic acid imidazolide A suspension of 114.5 g (0.495 mol) of 2-(4-aminophenyl)-4-hydroxy-5-pyrimidine carboxylic acid and 2.97 liters of dichloromethane is stirred at room temperature and 208 ml (1.48 mol) of triethylamine is added followed by 208 ml (1.63 mol) of trimethylsilyl chloride dropwise over 15 minutes. The mixture is allowed to stir at room temperature for 1.5 hrs and then added to the mixture below.

A suspension of 129.8 g (0.99 mol) of N-acetyl-L-alanine and 2.97 liters of acetonitrile is stirred at room temperature and 109 ml (0.99 mol) of N-methylmorpholine is added. The stirred mixture is cooled to −17° C. and 84.1 ml (0.99 mol) of methyl chloroformate is added dropwise at this temperature and the mixture is stirred at −15° for 30 minutes. The mixture is then cooled to −30° C. and the silylated mixture from above is added over a period of 5 minutes keeping the temperature at −15° C. The mixture is stirred for 4 hrs at 0° C. and allowed to stand overnight at room temperature. The reaction mixture is concentrated to a solid in vacuo and 4 liters of water is added to the residue. The pH of the suspension is adjusted to 7.5 with alkali and the solution is clarified by filtration. After three extractions with 300 ml portions of methylene chloride, the aqueous layer is acidified to pH 2 with 12% hydrochloric acid. The solid is removed by filtration and washed with water. The wet cake is then washed with 750 ml of isopropanol-ether (1:1) and then with ether and dried to give 147 g of 2-[4-(N-acetyl-L-alanylamino)phenyl]-4-hydroxy-5-pyrimidine carboxylic acid; mp 226° C. dec. $[\alpha]_D^{23} = -72.5°$ (cl, pH 8).

$E_1^1 632 \lambda 309 \ nm$ pH 7

A suspension of 2.38 grams (6.92 mmol) of the above acylated pyrimidine carboxylic acid and 10 ml of dimethylformamide is stirred at room temperature and 2.0 g (12.3 mmol) of carbonyldiimidazole is added. The stirred mixture is heated at 50°–60° C. for 1 hr and allowed to stand at room temperature for 3 hrs. The solvent is removed in vacuo and the residue is crystallized by the addition of dichloromethane. The product is filtered, washed with dichloromethane and ether, and dried to give 1.95 g of the title imidazolide; mp 222° C. dec.

F.
2-[4-(N-Acetyl-DL-alanylamino)phenyl]-4-hydroxy-5-pyrimidine carboxylic acid imidazolide The silylated derivative of 2-(4-aminophenyl)-4-hydroxy-5-pyrimidine carboxylic acid is prepared as described in Starting Material E from 11.55 g (50 mmol) of the acid, 20.8 ml (148 mmol) of triethylamine, and 20.8 ml (163 mmol) of trimethylsilyl chloride in 300 ml of dichloromethane.

A solution of 13.1 g (100 mmol) of DL-acetyl-alanine and 300 ml of acetonitrile is stirred at room temperature and 10.1 g (100 mmol) of N-methylmorpholine is added. After cooling to −15° C., 10.4 g (110 mmol) of methyl chloroformate is added and the reaction mixture is stirred for 30 min at −15° C. The above silylated solution is added and the mixture stirred overnight at room temperature. The mixture is evaporated to dryness in vacuo, 150 ml of water is added, and the pH is adjusted to 2.0 with hydrochloric acid. The solid is filtered, washed with water, isopropanol and ether and dried to give 15.5 g of 2-[4-(N-acetyl-DL-alanylamino)phenyl]-

4-hydroxy-5-pyrimidine carboxylic acid; mp 271°–272° C.

$E_1^1$635λ309 nm}pH 7

A suspension of 3.0 g (8.75 mmol) of the above acid and 30 ml of dimethylformamide is stirred at room temperature and 3.0 g (18.5 mmol) of carbonyldiimidazole is added. The reaction mixture is heated at 50°–60° C. for 0.5 hr and stirred at room temperature overnight. Dichloromethane (25 ml) and ether (50 ml) are added and the solid filtered, washed with ether, and dried to afford 3.2 g of the title imidazolide.

G.
2-[4-(N-Acetyl-alpha-aminoisobutyrylamino)phenyl]-4-hydroxy-5-pyrimidine carboxylic acid imidazolide A suspension of 41.2 g (0.4 mmol) of alpha-aminoisobutyric acid, 100 ml pyridine, and 100 ml water is stirred at 0°–5° C. and 45.0 ml (0.45 mmol) of acetic anhydride is added over a period of 30 min. Solution is observed after 1 hr and the mixture is allowed to stand at room temperature for 10 hrs. The reaction mixture is diluted with 500 ml water and evaporated in vacuo. The residue is then recrystallized from water, dried in vacuo affording 37.0 g N-acetyl-alpha-aminoisobutyric acid.

A mixture of 11.6 g (80 mmol) of N-acetyl-alpha-aminoiosbutyric acid 8.8 ml (80 mmol) of N-methylmorphorine, and 200 ml acetonitrile is cooled to −20° C., 6.0 ml (80 mmol) of methyl chloroformate is added. The mixture stirred at −10° C. to −5° C. for 20 minutes and a solution of the silylated 2-(4-aminophenyl)-4-hydroxy-5-pyrimidine carboxylic acid [prepared as described in Starting Material E from 9.2 g (40 mmol) of the acid, 16.8 ml (120 mmol) of triethylamine, and 15.4 ml (120 mmol) of trimethylsilyl chloride in 400 ml of dichloromethane] is added dropwise. After the addition, the mixture is stirred in an ice bath for 3 hrs, then at room temperature for 12 hrs. Two ml of isopropanol are added to the mixture and it stirred for 20 min and the solid filtered. The filtrate is evaporated in vacuo and the residue triturated in water, filtered, and dried to yield 5.6 g of 2-[4-(N-acetyl-alpha-aminoisobutyrylamino)-phenyl]-4-hydroxy-5-pyrimidine carboxylic acid.

A mixture of 5.6 g (15.7 mmol) of the above pyrimidine acid and 5.0 g (31 mmol) of carbonyldiimidazole in 100 ml tetrahydrofuran is stirred at 50° C. for ½ hr and at room temperature for 2 hrs. The mixture is filtered and the solids washed with ether and dried in vacuo affording 4.75 g of the title imidazolide.

H.
2-[4-(N-Acetyl-DL-prolylamino)phenyl]-4-hydroxy-5-pyrimidine carboxylic acid imidazolide A solution of 13.2 g (84 mmol) of N-acetyl-DL-proline in 150 ml of dichloromethane is stirred at −10° and 11.8 ml (84 mmol) triethylamine is added followed by 11.0 ml (84 mmol) of isobutyl chloroformate. The reaction mixture is stirred at −10° C.±5° C. for ½ hr and a cold solution of 12.94 g (56 mmol) of 2-(4-aminophenyl)-4-hydroxy-5-pyrimidine carboxylic acid and 8.6 ml (61.6 mmol) triethylamine in 200 ml N,N-dimethylacetamide is added. The reaction solution is stirred at 0°–5° C. for 3 hours and overnight at room temperature. The reaction mixture is evaporated and the residue triturated with water. The mixture is filtered to give 3.5 g of solid. On standing, more solid crystallizes out of the aqueous filtrate. Filtration gives an additional 11.5 g of 2-[4-(N-acetyl-DL-prolylamino)phenyl]-4-hydroxy-5-pyrimidine carboxylic acid; mp 269°–271° C. dec.

$E_1^1$590λ309 nm}pH 7

A mixture of 7.4 g (20 mmol) of 2-[4-(N-acetyl-DL-prolylamino)phenyl]-4-hydroxy-5-pyrimidine carboxylic acid and 6.48 g (40 mmol) of carbonyldiimidazole in 75 ml of tetrahydrofuran is stirred at 51°–52° for 1 hr and at room temperature overnight. The reaction mixture is filtered and the solid washed with tetrahydrofuran and ether giving 5.8 grams of the title imidazolide.

I.
2-[4-(N-Acetyl-beta-alanylamino)phenyl]-4-hydroxy-5-pyrimidine carboxylic acid imidazolide A solution of 4.6 g (35 mmol) of N-acetyl-beta-alanine, 100 ml acetonitrile, and 3.9 ml (35 mmol) of N-methylmorpholine is stirred at −15° C. and 5.0 ml (38.5 mmol) of isobutyl chloroformate is added. After 30 minutes at −15° C. a solution prepared from 4.05 g (17.5 mmol) of 2-(4-aminophenyl)-4-hydroxy-5-pyrimidine carboxylic acid, 7.35 ml (52.5 mmol) of triethylamine, and 7.96 ml (62.7 mmol) of trimethylsilyl chloride in 100 ml of dichloromethane is added and the mixture stirred at −10° C. for 1 hour and at room temperature overnight. The mixture is evaporated to near dryness in vacuo and treated with 200 ml of water. The product is precipitated by acidifying to pH 2.0 and is filtered, washed with water, isopropanol, ether, and dried to give 5.8 g of 2-[4-(N-acetyl-beta-alanylamino)phenyl]-4-hydroxy-5-pyrimidine carboxylic acid.

$E_1^1$642λ310 nm}ph 7.0

A suspension of 5.7 g (16.5 mmol) of the above pyrimidine acid, 20 ml of dimethylformamide, and 5.7 g (35.1 mmol) of carbonyldiimidazole is stirred at 50°–60° C. for 30 minutes and 3 hrs at room temperature. Acetonitrile (40 ml) and ether (40 ml) are added and the product filtered, washed with acetonitrile, ether, and dried to give 6.3 g of the title imidazolide.

J.
2-[4-(N-Acetyl-DL-methionylamino)phenyl]-4-hydroxy-5-pyrimidine carboxylic acid imidazolide A suspension of 14.34 g (75 mmol) of N-acetyl-DL-methionine and 150 ml of dichloromethane is stirred at −15° and 10.5 ml (75 mmol) of triethylamine is added followed by 9.75 ml (75 mmol) of isobutyl chloroformate. After stirring for 20 minutes at −15° C., a solution of 11.6 g (50 mmol) of 2-(4-aminophenyl)-4-hydroxy-5-pyrimidine carboxylic acid in 200 ml of dimethylacetamide containing 7.7 ml (55 mmol) of triethylamine is added at −15° C. The mixture is stirred at 0° C. for 3 hrs and overnight at room temperature. The mixture is evaporated and the residue triturated with water. The aqueous suspension, after adjusting the pH to 2.5 with dilute HCl is filtered, washed with water, and dried to give 11.54 g of 2-[4-(N-acetyl-DL-methionylamino)phenyl]-4-hydroxy-5-pyrimidine carboxylic acid; mp 259° C. dec.

$E_1^1$508λ309 nm}pH 7

A mixture of 2.04 g (4.9 mmol) of the above pyrimidine carboxylic acid, 1.6 g (9.8 mmol) of carbonyldiimidazole, and 25 ml of dimethylformamide is stirred at 50°–60° C. for 30 min and allowed to stand at room temperature overnight. The solvent is removed in vacuo and the residue treated with 50 ml of tetrahydrofuran and 200 ml of ether. The solid is filtered, washed with tetrahydrofuran, ether, and dried to give 2.04 of the title imidazolide.

K.

2-[4-(N-Acetyl-DL-leucylamino)phenyl]-4-hydroxy-5-pyrimidine carboxylic acid imidazolide A solution of 13.0 g (75 mmol) of N-acetyl-DL-leucine, 10.5 ml (75 mmol) of triethylamine, and 150 ml of dichloromethane is stirred at $-10°$ and 9.75 ml (75 mmol) of isobutyl chloroformate is added. The reaction mixture is stirred for ½ hour at $-10°$ C. and a cold solution of 11.6 g (50 mmol) of 2-[4-aminophenyl)-4-hydroxy-5-pyrimidine carboxylic acid and 7.7 (55 mmol) of triethylamine in 200 ml of dimethylformamide is added. The mixture is stirred at 5° C. for 3 hrs and overnight at room temperature. The reaction mixture is evaporated and the residue treated with water. The pH is lowered to 2.5 with dilute hydrochloric acid and the solid filtered, washed with water, and dried to give 13.8 g of 2-[4-(N-acetyl-DL-leucylamino)phenyl]-4-hydroxy-5-pyrimidine carboxylic acid; mp 233°–235° C. dec.

$E_1^1 434 \lambda 308$ nm}pH 7

A mixture of 3.86 g (10 mmol) of the above pyrimidine carboxylic acid and 3.24 g (20 mmol) of carbonyldiimidazole in 50 ml of dimethylformamide is stirred at 50°–60° C. for 30 min and allowed to stand at room temperature overnight. The solvent is removed in vacuo and the residue treated with 50 ml of ether. Filtration, washing with tetrahydrofuran and ether, and drying affords 1.90 g of the title imidazolide.

L.

2-[4-(N-Acetyl-DL-glutaminylamino)phenyl]-4-hydroxy-5-pyrimidine carboxylic acid imidazolide A solution of 14.1 g (75 mmol) of N-acetyl-L-glutamine and 9.75 ml (75 mmol) of triethylamine in 150 ml of dimethylformamide is stirred at $-15°$ to $-20°$ C. and 9.75 ml (75 mmol) of isobutylchloroformate is added. After stirring at $-15°$ to $-20°$ C. for 30 min a cold solution of 11.6 g (50 mmol) of 2-(4-aminophenyl)-4-hydroxy-5-pyrimidine carboxylic acid and 7.15 ml (50 mml) of N-methylmorpholine in 200 ml of dimethylformamide is added at $-15°$ C. The reaction mixture is stirred at $-15°$ for 20 min at 5° C. for 3 hrs, and at room temperature overnight. The reaction mixture is evaporated and the residue treated with water. The pH is lowered to 2.5 with hydrochloric acid and the solid is filtered, washed with water, and dried to afford 17.3 g of 2-[4-(N-acetyl-DL-glutaminylamino)phenyl]4-hydroxy-5-pyrimidine carboxylic acid; mp 247°–248° C. dec. $[\alpha]_{23}^D -2.8°$ (c0.7, DMSO)

$E_1^1 487 \lambda 310$ nm}pH 7

A mixture of 4.01 g (10 mmol) of the above pyrimidine carboxylic acid and 3.24 g (20 mmol) of carbonyldiimidazole in 50 ml of dimethylformamide is stirred at 50°–60° for 30 min and allowed to stand overnight at room temperature. The solvent is removed in vacuo and the residue treated with 50 ml of tetrahydrofuran and 200 ml of ether. The solid is filtered, washed with tetrahydrofuran and ether, and dried affording 2.38 g of the title imidazolide.

M.

2-[4-(N-Acetyl-L-hydroxyprolylamino)phenyl]-4-hydroxy-5-pyrimidine carboxylic acid N-hydroxysuccinimide ester The silylated derivative of 2-(4-aminophenyl)-4-hydroxy-5-pyrimidine carboxylic acid is prepared from 10 g (43.2 mmol) of the acid, 18.06 ml (130 mmol) of triethylamine, and 17.1 ml (130 mmol) of trimethylsilyl chloride in 800 ml of dichloromethane as described in Starting Material E.

A suspension of 22.4 g (129 mmol) of N-acetyl-L-4-hydroxyproline and 300 ml of dichloromethane is stirred at $-10°$ and 18.06 ml (130 mmol) of triethylamine is added, followed by 10.2 ml (130 mmol) of methyl chloroformate at $-10°$ to $-15°$ C. The silylated acid solution from above is added in aliquots keeping the temperature below $-5°$ C. When all is added, the reaction temperature is allowed to rise to 0° C. and the reaction flask is placed in an ice bath. The reaction is stirred overnight allowing the bath temperature to rise to room temperature. The reaction is filtered and filtrate is evaporated. Water is added to the residue and the mixture is stirred for 2 hrs and filtered. The product is resuspended in water, stirred, and filtered. The solid is taken up in isopropanol and a light precipitate is filtered off. The filtrate is evaporated down and the residue is washed with isopropanol and then ether. The product is suspended in water and cooled in an ice bath. The pH is adjusted to 2.15 with dilute hydrochloric acid and the precipitate is filtered. The solid is taken up in isopropanol and the insolubles filtered off. The solids are dissolved in methanol and added to the isopropanol solution. The resulting solution is evaporated down and ether added to the residue. A light yellow solid is obtained and dried under vacuum to give 8.8 g of 2-[4-acetyl-L-hydroxyprolylamino)phenyl]-4-hydroxy-5-pyrimidine carboxylic acid.

A solution of 3.0 g (7.8 mmol) of the above pyrimidine acid and 1.0 g (8.6 mmol) of hydroxysuccinimide in N,N-dimethylacetamide is stirred in an ice bath and 2.0 g (9.5 mmol) of dicyclohexylcarbodiimide in N,N-dimethylacetamide is added giving a total volume of 30 ml of N,N-dimethylacetamide. The reaction is stirred overnight. Ether is added to the reaction mixture and the resulting oil is triturated into a solid by the addition of isopropanol. The solid is filtered, washed with isopropanol and dried to give 2.11 g of the title activated ester.

N.

2-[4-(N,N'-Diacetyl-DL-lysylamino)phenyl]-4-hydroxy-5-pyrimidine carboxylic acid imidazolide The silylated derivative of 2-(4-aminophenyl)-4-hydroxy-5-pyrimidine carboxylic acid is prepared from 4.64 g (20 mmol) of the acid, 6.3 g (63 mmol) of triethylamine, and 6.8 g (63 mmol) of trimethylsilyl chloride in 160 ml of dichloromethane as described in Starting Material E.

A solution of 9.2 g (40 mmol) of N,N'-diacetyl-DL-lysine and 4.06 g (42 mmol) of N-methylmorpholine in 100 ml of 1:1 dimethylacetamide-dichloromethane is stirred at $-12°$ C. and 5.7 g (42 mmol) of isobutyl chloroformate is added. The mixture is stirred at $-12°$ C. for 25 min and the cold (5° C.) silylated acid solution from above is added over 30 min at $-12°$ C. After stirring at 5° C. for 2 hrs and at room temperature overnight, 15 ml of isopropanol is added and the solid is filtered washed with isopropanol and water was dried to give 7.1 g of 2-[4-(N,N'-diacetyl-DL-lysylamino)-phenyl]-4-hydroxy-5-pyrimidine carboxylic acid; mp 252°–253° C. dec.

A stirred suspension of 7.0 g (15.8 mmol) of the above pyrimidine carboxylic acid and 5.2 g (32 mmol) of carbonyldiimidazole in 125 ml of dimethylformamide is stirred at 50°–55° C. for 1 hr and at room temperature for 4 hrs. The product is precipitated by adding 500 ml

O.

2-[4-(N-Acetyl-γ-aminobutyrylamino)phenyl]-4-hydroxy-5-pyrimidine carboxylic acid imidizolide The silylated derivative of 2-(4-aminophenyl)-4-hydroxy-5-pyrimidine carboxylic acid is prepared as described in Starting Material E from 4.6 g (20 mmol) of the acid, 8.4 ml (60 mmol) of triethylamine, 7.7 ml (60) of trimethylsilyl chloride, in 150 ml of dichloromethane.

A suspension of 5.8 g (40 mmol) of N-acetyl-γ-aminobutyric acid and 100 ml of acetonitrile is stirred at room temperature and 5.6 ml (40 mmol) of triethylamine is added. The resulting solution is cooled to −20° C. and 3 ml (40 mmol) of methyl chloroformate is added. The reaction mixture is stirred at −10° to −5° C. for 30 min and the above ice cold silylated solution is added during a 30 min period. The reaction is stirred at 0°–5° C. for 4 hrs and at room temperature overnight. Isopropanol (3 ml) is added and the suspension stirred for 20 min. The solvents are evaporated and the residue is suspended in 100 ml of water and stirred for 20 min. The solid is filtered, washed with water, and dried to give 6.44 g of 2-[4-(N-acetyl-aminobutyrylamino)-phenyl]-4-hydroxy-5-pyrimidine carboxylic acid.

A suspension of 6.44 g (18 mmol) of the above acylated pyrimidine acid, 5.8 g (36 mmol) of carbonyldiimidazole, and 50 ml of N,N-dimethylacetamide is stirred at room temperature and solution is observed in 15 min. Within 40 min the product crystallizes and stirring is stopped after a total of 3 hrs. The reaction mixture is diluted with 100 ml of tetrahydrofuran and the solid is filtered, washed with ethyl acetate, and dried to give 6.01 g of the title imidazolide.

P.

2-[4-(N-t-Butoxycarbonyl-D-alanylamino)phenyl-4-hydroxy-5-pyrimidine carboxylic acid imidazolide A suspension of 13.28 g (57.5 mmol) of 2-(4-aminophenyl)-4-hydroxy-5-pyrimidine carboxylic acid and 200 ml of acetonitrile is stirred at room temperature and 16.0 ml (57.5 mmol) of triethylamine is added. The mixture is stirred at room temperature for 30 min and allowed to stand for an additional 30 min and is then added to the mixed anhydride below.

A solution of 21.75 g (0.115 mol) of N-t-butoxycarbonyl-D-alanine and 300 ml of acetonitrile is stirred at 0° C. and 27.5 ml (0.25 mol) of N-methylmorpholine is added. The mixture is stirred at 0° C. for 10 min, cooled to −30° and 13.87 g (0.115 mol) of pivaloyl chloride is added. The reaction mixture is stirred at −15° C. for 1 hr and the above pyrimidine acid solution is added slowly keeping the temperature below −10° C. The reaction is stirred at −10° C. for 3.5 hrs and allowed to come to room temperature overnight. The solvent is evaporated in vacuo and the residue suspended in 400 ml of water and the pH adjusted to 3.8 with solid citric acid. The solid is filtered, washed with water and ether, and dried to give 24.3 g of 2-[4-(N-t-butoxycarbonyl-D-analylamino)phenyl]-4-hydroxy-5-pyrimidine carboxylic acid. $[\alpha]_D^{23} + 31.4°$ (cl, pH 7).

$E_1^1$ 490λ308 nm

A solution of 4.0 g (10 mmol) of the above pyrimidine acid abd 30 ml of dimethylformamide is stirred at room temperature and 2.43 g (15 mmol) of carbonyldiimidazole is added. The reaction is stirred at room temperature for 18 hrs and the dimethylformamide evaporated under high vacuum. The residue is dissolved in 30 ml of dichloromethane and 70 ml of ether is added and the product precipitates as a gum. The solvents are decanted and the residue is stirred with 50 ml of acetonitrile until crystalline. Ether (50 ml) is added and the solid is filtered, washed with acetonitrile-ether (1:1), ether, and dried to give 4.1 g of the title imidazolide.

Q.

2-[4-((5-Oxo-DL-prolyl)amino)phenyl]-4-hydroxy-5-pyrimidine carboxylic acid

A suspension of 3.87 g (30 mmol) of 5-oxo-DL-proline, 2.3 ml (30 mmol) of dimethylformamide, and 50 ml of dichloromethane is stirred at 0°–5° C. and 2.2 ml (30 mmol) of thionyl chloride is added. Stirring is continued at 0°–5° C. for 1.67 hrs and a solution of 4.62 g (20 mmol) of 2-(4-aminophenyl)-4-hydroxy-5-pyrimidine carboxylic acid, 3.1 ml (22 mmol) of triethylamine and 60 ml of dimethylformamide is added. The reaction mixture is stirred at 0°–5° C. for 3 hrs and at room temperature overnight. The solid is filtered, washed with dichloromethane, methanol, and ether, and dried to give 4.94 g of 2-[4-((5-oxo-DL-prolyl)-amino)phenyl]-4-hydroxy-5-pyrimidine carboxylic acid.

A mixture of 4.88 g (14.25 mmol) of the above pyrimidine acid, 4.62 g (28.5 mmol) of carbonyldiimidazolide, and 25 ml of dimethylformamide is stirred at 45°–50° C. for 30 min and at room temperature overnight. Tetrahydrofuran (100 ml) and ether (50 ml) are added and a gummy solid precipitates. The solid is triturated with acetonitrile and filtered, washed with acetonitrile and ether, and dried to give 3.54 g of the title imidazolide.

R.

2-[4-(N-Acetyl-D-alanylamino)phenyl]-4-hydroxy-5-pyrimidine carboxylic acid imidazolide A suspension of 11.5 g (50 mmol) of 2-(4-aminophenyl)-4-hydroxy-5-pyrimidine carboxylic acid and 300 ml of dichloromethane is stirred at room temperature and 21.1 ml (150 mmol) of trimethylsilyl chloride is added. The mixture is stirred at room temperature for 1 hr and 12.4 ml (50 mmol) of bis(trimethylsilyl) acetamide is added.

A solution of 19.7 g (150 mmol) of acetyl-D-alanine and 400 ml of dichloromethane is stirred at 5° C. and 16.5 ml (150 mmol) of N-methylmorpholine is added. The reaction mixture is cooled to −20° C. and 12.0 ml (150 mmol) of methyl chloroformate is slowly added while keeping the temperature below −10° C. The reaction is stirred at −15° C. for 30 min and the above silylated mixture is added at −15°±5° C. The resulting mixture is stirred overnight as the ice bath melts. The solvents are evaporated and 300 ml of water is added to the residue and stirred for 1 hr. The solid is filtered, washed with water, isopropanol-ether (1:1), ether, and dried to give 13.4 g of 2-[4-(N-acetyl-D-alanylamino)-phenyl]-4-hydroxy-5-pyrimidine carboxylic acid; mp 217°–218° C. dec.

$[\alpha]_D^{23} + 80.5°$ (cl, pH 8.2)

A solution of 11.3 g (32.8 mmol) of the above pyrimidine acid and 160 ml of dimethylformamide is stirred at room temperature and 16.0 g (98.4 mmol) of carbonyldiimidazole is added. After 4 hrs at room temperature the dimethylformamide is evaporated under high vacuum at 45° C. to give an oily residue. Acetonitrile (300 ml) is added and solution is obtained by heating on a steam bath and a solid separates almost immediately. The mixture is cooled and the solid filtered, washed with acetonitrile, and dried to give 9.2 g of the title imidazolide.

S.
2-[4-(N-Acetyl-D-valylamino)phenyl]-4-hydroxy-5-pyrimidine carboxylic acid imidazolide A suspension of 11.41 g (71.7 mmol) of N-acetyl-D-valine and 150 ml of dichloromethane is stirred at room temperature and 7.9 ml (71.7 mmol) of N-methylmorpholine is added. The resulting solution is cooled to −10° C. and 9.3 ml (71.7 mmol) of isobutyl chloroformate is added. The reaction mixture is stirred at −15°±5° C. for 45 min and an ice cold solution of 11.09 g (48 mmol) of 2-(4-aminophenyl)-4-hydroxy-5-pyrimidine carboxylic acid, 7.4 ml (52.8 mmol) of triethylamine, and 200 ml of N,N-dimethylacetamide is added while keeping the temperature below −10° C. The mixture is stirred at 0°-5° C. for 2 hrs and overnight at room temperature. A small amount of solid is filtered and the filtrate is evaporated to dryness. Water is added to the residue and the resulting solid filtered, washed with water, ethyl acetate, and ether and dried to give 8.9 g of 2-[4-(N-acetyl-D-valylamino)phenyl]-4-hydroxy-5-pyrimidine carboxylic acid. A second crop, obtained from the aqueous filtrate, weighs 2.35 g. $[\alpha]_D^{23}$ +4.50 (c1, pH 7).

A mixture of 3.72 g (10 mmol) of the above pyrimidine acid, 3.24 g (20 mmol) of carbonyldiimidazole, and 25 ml of dimethylformamide is stirred at 49°-52° C. for 30 min. The solution is treated with 50 ml of tetrahydrofuran and 200 ml of ether and stored in the cold overnight. The solid is filtered, washed with ether and dried to give 2.63 g of the title imidazolide.

T.
2-[4-(N-t-butoxycarobonyl-L-glutaminylamine)-phenyl]-4-hydroxy-5-pyrimidine carboxylic acid imidazolide A suspension of 5.78 g (25 mmol) of 2-(4-aminophenyl)-4-hydroxy-5-pyrimidine carboxylic acid and 100 ml of acetonitrile is stirred at room temperature and 5.25 g (52 mmol) of triethylamine is added. The mixture is stirred for 1 hr and the resulting solution is added to a solution of mixed anhydride prepared as follows. A suspension of 9.24 g (37.5 mmol) of N-t-butoxycarbonyl-L-glutamine and 200 ml of acetonitrile is stirred at 0° C. and 7.58 g (75 mmol) of N-methylmorpholine is added. The resulting solution is cooled to −30° C. and 4.52 g (37.5 mmol) of pivaloyl chloride is added and stirring is continued at −10°±5° C. for 1 hr. The pyrimidine acid solution is added, keeping the temperature below −10° C., and stirring is continued for 2 hrs and the reaction is placed in an ice bath and allowed to warm to room temperature overnight. The solvent is evaporated and the residue dissolved in ice water. The pH is adjusted to 3.2 with solid citric acid and the resulting precipitate is filtered, washed with water, and redissolved in ethanol. The solution is clarified by filtration and the filtrate evaporated. The residue is triturated with ether, filtered, and the precipitate washed with ether, and dried to give 7.5 g of 2-[4-(N-t-butoxycarbonyl-L-glutaminylamino)phenyl]-4-hydroxy-5-pyrimidine carboxylic acid; $[\alpha]_D^{23}$ −16° (c1, pH 7).

$E_1^1$ 452λ309 nm pH 7

A suspension of 2.0 g (4.35 mmol) of above pyrimidone acid, 2.0 g (12.3 mmol) of carbonylidiimidazole, and 75 ml of acetonitrile is stirred at 50°-60° C. for 2 hrs. The solvent is evaporated under reduced pressure and the residue triturated with 1:1 tetrahydrofuran ether. The solvent is decanted and replaced with fresh solvent and the trituration process repeated until a fine powder develops. The powder is removed by filtration, washed with 1:1 tetrahydrofuran ether, ether, and dried to give 1.8 g of the title imidazolidie.

U.
2-[4-[(2-Oxo-1-pyrrolidinyl)acetylamino]phenyl]-4-hydroxy-5-pyrimidine carboxylic acid imidazolide A suspension of 8.1 g (35 mmol) of 2-(4-aminophenyl)-4-hydroxy-5-pyrimidine carboxylic acid and 75 ml of N,N-dimethylacetamide is stirred at room temperature and 12 ml (85 mmol) of triethylamine is added. The mixture is stirred for 2 hrs until a solution forms.

In a separate flask 7.2 g (50 mml) of 2-oxo-1-pyrrolidineacetic acid is added to 150 ml of dichloromethane and 50 ml of a 1 M solution of 2-chloro-1-methylpyridinium methylsulfate in dichloromethane.* The mixture is stirred at room temperature and 7 ml (50 mmol) of triethylamine is added in portions, a solution results after ca. 2 hrs of stirring. The two solutions are combined and kept at room temperature for 48 hrs. The dichloromethane is evaporated and the residue is slurried with 700 ml water and brought into solution by adjusting to pH 8 with triethylamine. The pH is then lowered to 3.0 and the precipitated solid is collected, washed with water and acetone and dried to give 12.3 g of 2-[4-[(2-oxo-1-pyrrolidinyl)acetylamino]phenyl]-4-hydroxy-5-pyrimidine carboxylic acid as a pale yellow solid; mp > 320° C.

$E_1^1$ 600λ309 nm pH 7

*A stock solution of the coupling reagent can be made conveniently by mixing 38 ml (0.4 mol) 2-chloropyridine and 38 ml (0.4 mol) dimethylsulfate in 340 ml dichloromethane and allowing the bottled solution to react at room temperature for 2 days.

A suspension of 6.2 g (17 mmol) of the above pyrimidine acid, 4.9 g (30 mmol) of carbonyldiimidazole and 60 ml of N,N-dimethylacetamide is stirred overnight at room temperature. The mixture is diluted with 100 ml of dichloromethane and the solid is filtered, washed with dichloromethane, and dried to give 7.0 g of the title imidazolide; mp 245°-250° C.

We claim:

1. A compound of the formula

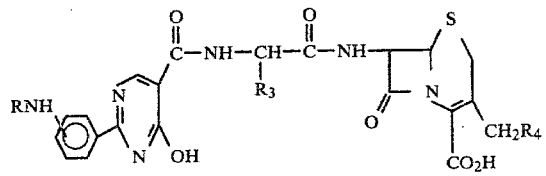

and pharmaceutically-acceptable salts thereof; wherein R is

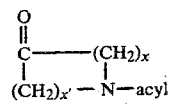

or $R_1[NR_5\text{-acyl}]_n$; x is an integer of from one to five; x' is zero, one or two and $R_1$ is hydrogen, lower alkyl, benzyl or

wherein $R_2$ is hydrogen, amino or a lower alkyl group of from one to four carbon atoms, wherein said carbon fragment is unsubstituted or substituted by from one to three chlorine or fluorine atoms; $R_5$ is hydrogen or lower alkyl and N-acyl is an aminoacyl moiety derived from a carboxylic acid of from two to ten carbon atoms wherein said aminoacyl moiety is unsubstituted or substituted by from one to three substituents selected from the group comprising hydroxyl, carboxyl,

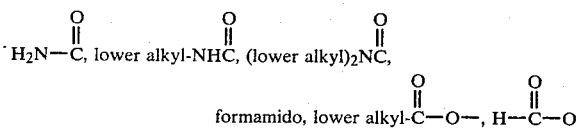

amino, lower alkylamido carbamido, carbonyl oxygen, lower alkoxy, lower alkylthio or sulfonic acid; n is an integer of from one to four; $R_3$ is phenyl, 4-hydroxyphenyl, 2-thienyl or cyclohexa-1,4-dien-1-yl and $R_4$ is acetoxy, carbamoyloxy or a heterocyclicthio group where the heterocyclic moiety is unsubstituted or substituted by a methyl group and the heterocycle is a thiadiazolyl, triazolyl or tetrazolyl group or the hetercyclicthio group has the formula

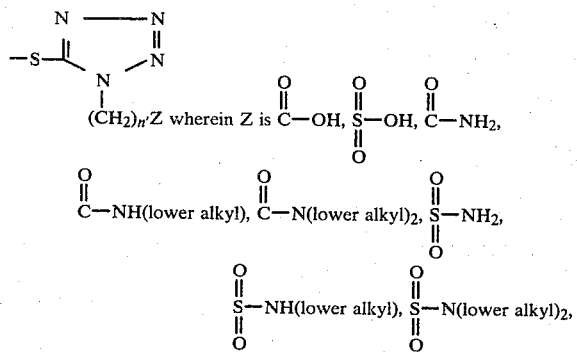

or $CH_2\text{-OH}$ and n' is an integer of from one to four.

2. The compounds of claim 1 wherein RNH is in the para position.

3. The compounds of claim 2 wherein the optically active R-NH fragment is in the D form.

4. The compounds of claim 2 wherein NH-acyl is D-alanyl, L-alanyl, DL-glutaminyl, L-hydroxyprolyl or DL-lysyl.

5. The compounds of claim 4 wherein $R_2$ is a carbon fragment of from one to two carbon atoms, and $R_5$ is hydrogen.

6. The compounds of claim 5 wherein $R_3$ is phenyl or 4-hydroxyphenyl.

7. The compounds of claim 6 wherein $R_4$ is acetoxy or a heterocyclicthio group wherein the heterocyclic group is a tetrazole and n is one and Z is hydroxy or carboxyl.

8. The compounds of claim 1 having the name N-[2-[4-(N-acetyl-D-alanylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

9. The compounds of claim 1 having the name N-[2-[4-(N-acetyl-alpha-aminoisobutyrylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

10. The compounds of claim 1 having the name N-[2-[4-(N-acetyl-beta-alanylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

11. The compounds of claim 1 having the name N-[2-[4-N-acetyl-DL-leucylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

12. The compounds of claim 1 having the name N-[2-[4-(N-acetyl-DL-methionylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

13. The compounds of claim 1 having the name N-[2[4-[(5-oxo-DL-prolyl)amino]phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

14. The compounds of claim 1 having the name N-[2-[4-(N-acetylglycylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

15. The compounds of claim 1 having the name N-[2-[4-(N-acetyl-DL-alanylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

16. The compounds of claim 1 having the name N-[2-[4-(N-acetyl-DL-alanylamino)phenyl]-4-hydroxy-5-pyrimidinylcarbonyl]-7-[D-2-amino-2-(4-hydroxyphenyl)acetamido]-3-acetoxymethyl-3-cephem-4-carboxylic acid and pharmaceutically-acceptable salts thereof.

17. The compounds of claim 1 having the name N-[2-[4-(N-acetyl-L-alanylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

18. The compounds of claim 1 having the name N-[2-]4-(N-acetyl-D-alanylamino)phenyl]-4-hydroxy-5-pyrimidinylcarbonyl]-7-[D-2-amino-2-(4-hydroxyphenyl)acetamido]-3-acetoxymethyl-3-cephem-4-carboxylic acid and pharmaceutically-acceptable salts thereof.

19. The compounds of claim 1 having the name N-[2-[4-($N^\alpha,N^\omega$-diacetyl-DL-lysylamino)phenyl]-4-hydroxy-5-pyrimidinyl-carbonyl]-7-[D-2-amino-2-phenylacetamido]-3-acetoxymethyl-3-cephem-4-carboxylic acid and pharmaceutically-acceptable salts thereof.

20. The compounds of claim 1 having the name N-[2-[4-(N-acetyl-DL-proplylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

21. The compound of claim 1 having the name N-[2-[4-(N-acetyl-DL-glutaminylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

22. The compounds of claim 1 havisng the name N-[2-[4-(N-acetyl-L-hydroxyprolylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

23. The compounds of claim 1 having the name N-[2-[4-(N-acetyl-γ- aminobutyrylamino)phenyl]-4-hydroxy-5-pyrimidinylcarbonyl]-7-[D-2amino-2-phenylacetamido]-3-acetoxymethyl-3-cephem-4-carboxylic acid and pharmaceutically-acceptable salts thereof.

24. The compounds of claim 1 having the name N-[2-[4-(N-acetyl-D-valylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

25. The compounds of claim 1 having the name N-[2-[4-(D-alanylamino)phenyl]-4-hydroxy-5-pyrimidinylcarbonyl]-7-[D-2-amino-2-phenylacetamido]-3-acetoxymethyl-3-cephem-4-carboxylic acid and pharmaceutically-acceptable salts thereof.

26. The compounds of claim 1 having the name N-[2-[4-(N-acetyl-D-alanylamino)phenyl]-4-hydroxy-5-pyrimidinylcarbonyl]-7-[D-2-amino-2-(2-thienyl)acetamido]-3-acetoxymethyl-3-cephem-4-carboxylic acid and pharmaceutically-acceptable salts thereof.

27. The compounds of claim 1 having the name N-[2-[4-(N-acetyl-DL-alanylamino)phenyl]-4-hydroxy-5-pyrimidinylcarbonyl]-7-[D-2-amino-2-phenylacetamido]-3-carbamoyloxymethyl-3-cephem-4-carboxylic acid and pharmaceutically-acceptable salts thereof.

28. The compounds of claim 1 having the name N-[2-[4-(N-acetyl-D-alanylamino)phenyl]-4-hydroxy-5-pyrimidinylcarbonyl]-7-[D-2-amino-2-phenylacetamido]-3-carbamoyloxymethyl-3-cephem-4-carboxylic acid and pharmaceutically-acceptable salts thereof.

29. The compounds of claim 1 having the name N-[2--[4-(N-acetylglycylamino)phenyl]-4-hydroxy-5-pyrimidinylcarbonyl]-7-[D-2-amino-2-phenylacetamido]-3-[[(1-methyl-1H-tetrazol-5-yl)-thio]-methyl]-3-cephem-4-carboxylic acid and pharmaceutically-acceptable salts thereof.

30. The compounds of claim 1 having the name N-[2-[4-(N-acetyl-DL-glutaminylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid and pharmaceutically-acceptable salts thereof.

31. The compounds of claim 1 having the name N-[2-[4-(N-acetyl-DL-alanylamino)phenyl]-4-hydroxy-5-pyrimidinylcarbonyl]-7-[D-2-amino-2-phenylacetamido]-3-[[(1-methyl-1H-tetrazol-5-yl)-thio]-methyl]-3-cephem-4-carboxylic acid and pharmaceutically-acceptable salts thereof.

32. The compounds of claim 1 having the name N-[2-[4-(N-acetyl-D-alanylamino)phenyl]-4-hydroxy-5-pyrimidinylcarbonyl]-7-[D-2-amino-2-phenylacetamido]-3-[[(1-methyl-1H-tetrazol-5-yl)-thio]-methyl]-3-cephem-4-carboxylic acid and pharmaceutically-acceptable salts thereof.

33. The compounds of claim 1 having the name N-[2-[4-(N-acetyl-L-alanylamino)phenyl]-4-hydroxy-5-pyrimidinylcarbonyl]-7-[D-2-amino-2-phenylacetamido]-3-[[(1-methyl-1H-tetrazol-5-yl)-thio]-methyl]-3-cephem-4-carboxylic acid and pharmaceutically-acceptable salts thereof.

34. The compounds of claim 1 having the name N-[2-[4-(N-acetyl-γ-aminobutyrylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid and pharmaceutically-acceptable salts thereof.

35. The compounds of claim 1 having the name N-[2--[4-(N-acetyl-alpha-aminoisobutyrylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid and pharmaceutically-acceptable salts thereof.

36. The compounds of claim 1 having the name N-[ 2-[4-(N-acetyl-D-valylamino)phenyl]-4-hydroxy-5-pyrimidinylcarbonyl]-7-[D-2-amino-2-phenylacetamido]-3-[[(1-methyl-1H-tetrazol-5-yl)-thio]-methyl]-3-cephem-4-carboxylic acid and pharmaceutically-acceptable salts thereof.

37. The compounds of claim 1 having the name N-[2-[4-(N-acetyl-L-hydroxyprolylamino)phenyl]-4-hydroxy-5-pyrimidinylcarbonyl]-7-[D-2-amino-2-phenylacetamido]-3-[[(1-methyl-1H-tetrazol-5-yl)thio]-methyl]-3-cephem-4-carboxylic acid and pharmaceutically-acceptable salts thereof.

38. The compounds of claim 1 having the name N-[2-[4-(N-acetyl-D-alanylamino)phenyl]-4-hydroxy-5-pyrimidinylcarbonyl]-7-[D-2-amino-2-(4-hydroxyphenyl)acetamido]-3-[[(1H-methyl-1H-tetrazol-5yl)thio]methyl]-3-cephem-4-carboxylic acid and pharmaceutically-acceptable salts thereof.

39. The compounds of claim 1 having the name N-[2-[4-(N-acetyl-DL-alanylamino)phenyl]-4-hydroxy-b 5-pyrimidinylcarbonyl]-7-[D-2-amino-2-(4-hydroxyphenyl)acetamido]-3-[[(1H-tetrazol-5-yl)thio]methyl]-3-cephem-4-carboxylic acid and pharmaceutically-acceptable salts thereof.

40. The compounds of claim 1 having the name N-[2-[4-(N-acetyl-L-alanylamino)phenyl]-4-hydroxy-5-pyrimidinylcarbonyl]-7-[D-2-amino-2-phenylacetamido]-3-[[(1-carboxymethyl-1H-tetrazol-5-yl)thio]methyl]-3-cephem-4-carboxylic acid and pharmaceutically-acceptable salts thereof.

41. The compounds of claim 1 having the name N-[2-[4-(N-acetyl-D-alanylamino)phenyl]-4-hydroxy-5-pyrimidinylcarbonyl]-7-[D-2-amino-2-phenylacetamido]-3-[[(1-carboxymethyl-1H-tetrazol-5-yl)thio]methyl]-3-cephem-4-carboxylic acid and pharmaceutically-acceptable salts thereof.

42. The compounds of claim 1 having the name N-[ 2-[4-(N-acetyl-DL-alanylamino)phenyl]-4-hydroxy-5-pyrimidinylcarbonyl]-7-[D-2-amino-2-phenylacetamido]-3-[[(1-carboxymethyl-1H-tetrazol-5- yl)thio]methyl]-3-cephem-4-carboxylic acid and pharmaceutically-acceptable salts thereof.

43. The compounds of claim 1 having the name N-[2-[4-(N-acetyl-L-hydroxyprolylamino)phenyl]-4-hydroxy-5-pyrimidinyl-carbonyl]-7-[D-2-amino-2-phenylacetamido]-3-[[(1-carboxymethyl-1H-tetrazol-5-yl)thio]methyl]-3-cephem-4-carboxylic acid and pharmaceutically-acceptable salts thereof.

44. The compounds of claim 1 having the name N-[2-[4-(N-acetyl-D-alanylamino)phenyl]-4-hydroxy-5-pyrimidinylcarbonyl]-7-[D-2-amino-2-(4-hydroxyphenyl)acetamido]-3-[[(1-carboxymethyl-1H-tetrazol-5-yl)thio]methyl]-3-cephem-4-carboxylic acid and pharmaceutically-acceptable salts thereof.

45. The compounds of claim 1 having the name N-[2-[4-(D-alanylamino)phenyl]-4-hydroxy-5-pyrimidinylcarbonyl]-7-[D-2-amino-2-phenylacetamido]-3-[[(1-carboxymethyl-1H-tetrazol-5-yl)-thio]methyl]-3-cephem-4-carboxylic acid and pharmaceutically-acceptable salts thereof.

46. The compounds of claim 1 having the name N-[2-[4-(N-acetlyglycylamino)phenyl]-4-hydroxy-5-pyrimidinylcarbonyl]-7-[D-2-amino-2-phenylacetamido]-3-[[(5-methyl-1,3,4-thiadiazol-2-yl)thio]methyl-3-cephem-4-carboxylic acid and pharmaceutically-acceptable salts thereof.

47. The compounds of claim 1 having the name N-[2-[4-(N-acetyl-DL-alanylamino)phenyl]-4-hydroxy-5-pyrimidinylcarbonyl]-7-[D-2-amino-2-phenylacetamido]-3-[[(5-methyl-1,3,4-thiadiazoyl-2-yl)thio]methyl]-3-cephem-4-carboxylic acid and pharmaceutically-acceptable salts thereof.

48. The compounds of claim 1 having the name N-[2-[4-(L-glutaminylamino)phenyl]-4-hydroxy-5-pyrimidinylcarbonyl]-7-[D-2-amino-2-phenylacetamido]-2-[[(1-carboxymethyl-1H-tetrazol-5-yl)methyl]-3-cephem-4-carboxylic acid and pharmaceutically-acceptable salts thereof.

49. The compounds of claim 1 having the name N-[2-[4-[(2-oxo-1-pyrrolidinyl)acetylamino]phenyl]-4-hydroxy-5-[[(1-carboxymethyl-1H-tetrazol-5-yl)thio]-methyl]-3-cephem-4-carboxylic acid and pharmaceutically-acceptable salts thereof.

50. A pharmaceutical composition comprising from 50 mg to 1000 mg of a compound of claim 1 and a pharmaceutical carrier.

51. A method for treating infections which comprises administering the pharmaceutical composition of claim 50.

* * * * *